United States Patent
Wells et al.

(10) Patent No.: US 10,417,932 B2
(45) Date of Patent: Sep. 17, 2019

(54) BIOMETRIC DATA GATHERING

(71) Applicants: John Andrew Wells, Paradise Valley, AZ (US); Michael Cummings, Carlsbad, CA (US)

(72) Inventors: John Andrew Wells, Paradise Valley, AZ (US); Michael Cummings, Carlsbad, CA (US)

(73) Assignee: J. A. Wells and Associates L.L.C, Paradise Valley, AZ (US)

( * ) Notice: Subject to any disclaimer, the term of this patent is extended or adjusted under 35 U.S.C. 154(b) by 291 days.

(21) Appl. No.: 15/731,379

(22) Filed: Jun. 5, 2017

(65) Prior Publication Data

US 2017/0278419 A1    Sep. 28, 2017

Related U.S. Application Data

(62) Division of application No. 14/121,226, filed on Aug. 14, 2014, now Pat. No. 9,704,412.

(51) Int. Cl.
*A63B 24/00* (2006.01)
*G09B 19/00* (2006.01)
(Continued)

(52) U.S. Cl.
CPC .......... *G09B 19/003* (2013.01); *A61B 5/1123* (2013.01); *A61B 5/6823* (2013.01); *A61B 5/6824* (2013.01); *A61B 5/6829* (2013.01); *G01C 22/006* (2013.01); *G06F 19/3481* (2013.01); *G09B 19/0038* (2013.01); *G09B 23/288* (2013.01); *A61B 5/002* (2013.01); *A61B 5/0022* (2013.01); *A61B 5/0205* (2013.01); *A61B 5/02438* (2013.01); *A61B 5/222* (2013.01); *A61B 5/224* (2013.01); *A61B 5/486* (2013.01); *A61B 5/4866* (2013.01); *A61B 5/6831* (2013.01); *A61B 5/6895* (2013.01); *A61B 2503/10* (2013.01); *A61B 2560/0475* (2013.01); *A61B 2562/0219* (2013.01); *G01P 15/00* (2013.01)

(58) Field of Classification Search
CPC .............. G09B 19/003; G09B 19/0038; G09B 23/288; A61B 5/1123; A61B 5/6823; A61B 5/6824; A61B 5/6829; A61B 15/00; A61B 2503/10; A61B 2560/0475; A61B 2562/0219; G01C 22/006; G06F 19/3481
USPC ........................................................ 434/247
See application file for complete search history.

(56) References Cited

U.S. PATENT DOCUMENTS 6,453,111 B1    9/2002  Sklar et al.
6,740,007 B2    5/2004  Gordon et al.
(Continued)

*Primary Examiner* — Robert P Bullington

(57) ABSTRACT

A universal 6-DOF mems sensor combined with six degree of motion algorithms and human motion parameters permits individualized real time motion analysis of a user to enable accurate measurements. Data derived thereby is wirelessly sent for viewing to a Bluetooth® enabled smartphone or combination smartphone and eyeglass device, such as the Google Glass® headset. The sensor is worn on a wrist or ankle band or in combination with a chest mounted cardio heart rate monitor dependent on the biometric parameters measured. Typical physical exercise data gathered includes reps, sets, 10-100 yard dash times, vertical, horizontal and broad jump distances, a range of shuttle times, RAST, steps taken, distance traveled, velocity, acceleration, and calories burned. The heart rate monitor provides cardio assessment and the 6-DOF sensor measures a runner's pace and cadence data.

15 Claims, 30 Drawing Sheets

(51) Int. Cl.

| | |
|---|---|
| *G01C 22/00* | (2006.01) |
| *A61B 5/11* | (2006.01) |
| *A61B 5/00* | (2006.01) |
| *G09B 23/28* | (2006.01) |
| *G06F 19/00* | (2018.01) |
| *G01P 15/00* | (2006.01) |
| *A61B 5/22* | (2006.01) |
| *A61B 5/0205* | (2006.01) |
| *A61B 5/024* | (2006.01) |

(56) References Cited

U.S. PATENT DOCUMENTS

| | | |
|---|---|---|
| 7,927,216 B2 | 4/2011 | Ikeda |
| 8,776,418 B1 | 7/2014 | Martinez et al. |
| 2008/0090703 A1 | 4/2008 | Rosenburg |
| 2008/0103023 A1 | 5/2008 | Chung et al. |
| 2008/0300055 A1 | 12/2008 | Lutnick |
| 2009/0075782 A1 | 3/2009 | Joubert et al. |
| 2012/0157263 A1 | 6/2012 | Sivak |
| 2014/0270711 A1 | 9/2014 | Maser |
| 2014/0280156 A1 | 9/2014 | Maser |
| 2015/0265903 A1 | 9/2015 | Kolen |
| 2015/0309563 A1 | 10/2015 | Conner |

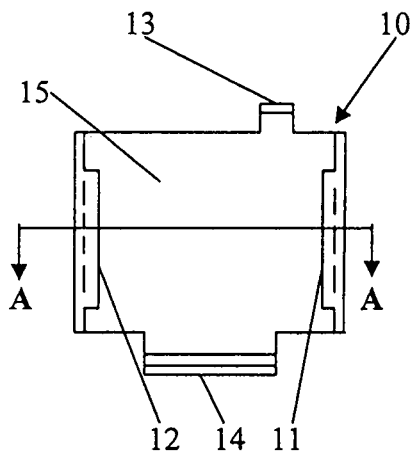
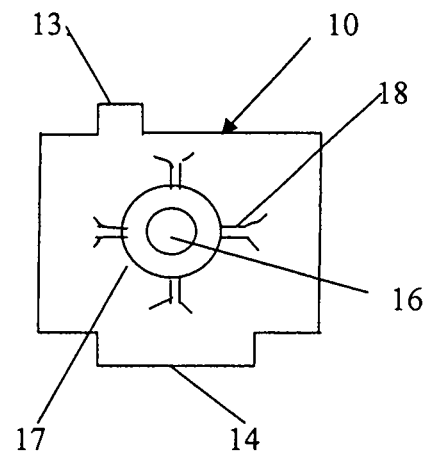
FIG. 3        FIG. 4
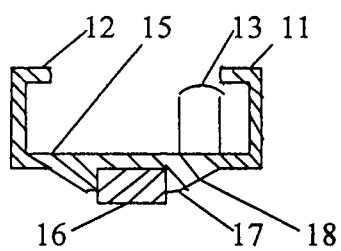
FIG. 3A
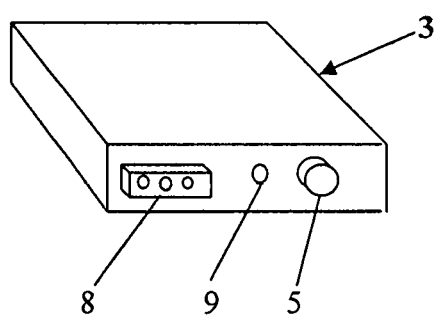
FIG. 5

| Signup | STEP 1 | Next | C |
|---|---|---|---|
| Short text explaining the goal of this signup, steps that are taken and why answers are needed ||| U R S E R |
| First Name | | Last Name | |
| email |||| 
| Repeat email |||| 
| Gender | Male | Female | Transgender |
| Other Information: e.g.  Sports Engaged in     Drop Down Menu  Diet Preferences     Drop Down Menu ||||
| Address  Street  City/County  State                    Zip  Country ||||

FIG. 7

| Previous | STEP 3 | Submit |
|---|---|---|

| Where do you train? | Gym | Home | Indoor | Outdoor |
|---|---|---|---|---|

Some exercises may not be available at your location, please use the drop down menu to select other exercises that are recommended as substitutions if you do not have the equipment or cannot perform that exercise. Also, please improve our exercise database by adding or sending us exercises that you would like us to add to our extensive database and put in the programs offered.

Please click on one or more of the following
Mode of Training:

- Tactical
- Athletic
- Weight Loss
- Body Building
- Health + Wellness
- Endurance Athlete

| Height | Weight | Age |
|---|---|---|

Are You: Athletic / Non-Athletic

Level of Experience: Low / Medium / High

CURSRSER

FIG. 9

| Previous | STEP 4 | Next |
|---|---|---|

Membership Sign up:

1. Membership level is selected for fitness website.

2. Payment type is selected.

☐ Check   ☐ Credit/Debit Card   ☐ Virtual Currency (Bitcoin)

3. Jawku product kit ordered consisting of a sensor module 3, Fitbands for wrist and ankle, chest strap with sensor module holder, and magnetic holder for attaching sensor module to weights and optionally a chest mounted heart rate sensor 4. User receives and activates 6DOF sensor module sequentially on wrist, ankle and chest and performs cardio and weight lifting exercises following specified directions to provide the cardio and weight lifting assessment.

5. User sends biometric data gathered via smartphone or computer to social fitness website.

FIG. 10

Friday (mm.dd.yy)
Bench Press

| | |
|---|---|
| Number of Sets | 5 |
| Number of Reps | 8 |
| Break between Sets | 1 minute |
| Break after Exercise | 1 minute |

Ready Stop

| Set | Reps | Weight (lbs) |
|:---:|:---:|:---:|
| 1 | 8 | 100 |
| 2 | 8 | 120 |
| 3 | 8 | 140 |
| 4 | 8 | 120 |
| 5 | 8 | 100 |

| Profile | Workouts | Calendar | Store |

FIG. 14

Friday (mm.dd.yy)

Bench Press

Exercise Summary

| Set | Reps | Weight (lbs) |
|-----|------|--------------|
| 1   | 8    | 100          |
| 2   | 8    | 120          |
| 3   | 8    | 140          |
| 4   | 8    | 120          |
| 5   | 8    | 100          |

Additional Data Goes Here

View Goals & History

| Profile | Workouts | Calendar | Store |

FIG. 15

Bench Press

Available Goals:

- Increase Weight
- Increase Number of Reps

| | |
|---|---|
| Current Goal: | nn lbs/not selected |
| | nn reps/not selected |
| Goal Date: | mm.dd.yy/not selected |
| New Goal: | nn lbs/not selected |
| | nn reps/not selected |
| New Date: | mm.dd.yy/not selected |

Submit

| Profile | Workouts | Calendar | Store |
|---|---|---|---|

FIG. 17

Goals

40 Yard Dash

| Goal Time | Goal Date | Current |
|---|---|---|
| nn seconds | mm.dd.yy | mm seconds |

Vertical Jump

| Goal | Goal Date | Current |
|---|---|---|
| nn seconds | mm.dd.yy | mm seconds |

Horizontal/Broad Jump

| Goal Distance | Goal Date | Current |
|---|---|---|
| nn seconds | mm.dd.yy | mm seconds |

Bench Press

| Goal Weight | Goal Date | Current |
|---|---|---|
| nn lbs | mm.dd.yy | mm lbs |
| Goal Reps | Goal Date | Current |
| n | mm.dd.yy | m |

| Profile | Workouts | Calendar | Store |
|---|---|---|---|

FIG. 18

Bench Press

Primary Muscle Group: Pectorals, Shoulders ...

Favorite Locations: gym, outdoors, home, church ...

Equipment: weight bench, barbell, dumbbell, Olympic weights ...

Exercise Description: User attaches 6DOF magnetic module to weight and while lying down on the bench on their back lowers the weight to chest level, then pushes the weight back up until the arm is straight. In the sport of power lifting the barbell bench press is one of the three lifts used extensively and is used by the NFL Scouting Combine. User manually enters weight size and reps into smartphone app.

Bench Press Video

Any other data needed

Add to workout    Substitute for workout

| Profile | Workouts | Calendar | Store |

FIG. 22

Sprint = 1 block of effort

Interval set = grouping of intervals

JAWKU Tests
Check your fitness with our tests ↓

40 yard Dash

Your current best score 125 ⇒

Bench Press

Your current best score 170 ⇒

Vertical Jump

Your current best score 846 ⇒

Proagility 5-10-5

Your current best score 762 ⇒

Broad Jump

Your current best score 521 ⇒

3 Cone Drill/ L-Drill

Your current best score 966 ⇒

Profile page
Your information and JAWKU Score ↑

FIG. 24

| Reps | % 1RM |
|---|---|
| 1 | 100 |
| 2 | 95 |
| 3 | 90 |
| 4 | 88 |
| 5 | 86 |
| 6 | 83 |
| 7 | 80 |
| 8 | 78 |
| 9 | 76 |
| 10 | 75 |
| 11 | 72 |
| 12 | 70 |

FIG. 28

| % | Weight |
|---|---|
| 60 | 93 |
| 70 | 110 |
| 80 | 125 |
| 85 | 130 |
|  |  |
|  |  |
|  |  |

FIG. 29

| Bench Press Exercise | Reps | Lbs Lifted | 1 Rep Max | 1 Rep Max Unload |
|---|---|---|---|---|
| Flat Barbell | | | | |
| Incline Barbell | | | | |
| Flat Dumbbell | | | | |
| Incline Dumbbell | | | | |

FIG. 30

| Bench Press Exercise | Reps | Lbs Lifted | 1 Rep Max | 1 Rep Max Unload |
|---|---|---|---|---|
| Flat Barbell | 5 | 315 | 367 | 235 |
| Incline Barbell | 5 | 315 | 294 | 188 |
| Flat Dumbbell | 5 | 315 | 165 | 105.6 |
| Incline Dumbbell | 5 | 315 | 132 | 84.5 |

FIG. 31

Male Age 12 Jawku Score & Percentile Rank

| Percentile Rank | Vertical Jump Inches | Broad Jump Inches | Pro-Agility Shuttle Seconds | 10-Yard Dash Seconds | 40 Yard Dash Seconds | Bench Press | Jawku Score |
|---|---|---|---|---|---|---|---|
| 99 | 16.5< | 7'5"< | 4.85> | 1.97> | 5.28> | 38> | 10.75 |
| 95 | 16.25 | 7'4" | 4.86-4.87 | 1.98-1.99 | 5.29-5.30 | 37 | 10.5 |
| 92.5 | 16 | 7'3" | 4.88-4.89 | 2.00-2.01 | 5.31-5.32 | 36 | 10.25 |
| 90 | 15.75 | 7'2" | 4.90-4.91 | 2.02-2.03 | 5.33-5.34 | 35 | 10 |
| 87.5 | 15.5 | 7'1" | 4.92-4.93 | 2.04-2.05 | 5.35-5.36 | 34 | 9.75 |
| 85 | 15.25 | 7' | 4.94-4.95 | 2.06-2.07 | 5.37-5.38 | 33 | 9.5 |
| 82.5 | 15 | 6'11" | 4.96-4.97 | 2.08-2.09 | 5.39-5.40 | 32 | 9.25 |
| 80 | 14.75 | 6'10" | 4.98-4.99 | 2.10-2.11 | 5.41-5.42 | 31 | 9 |
| 77.5 | 14.5 | 6'8" | 5.00-5.01 | 2.12-2.13 | 5.43-5.44 | 30 | 8.75 |
| 75 | 14.25 | 6'6" | 5.02-5.03 | 2.14-2.15 | 5.45-5.46 | 29 | 8.5 |
| 72.5 | 14 | 6'5" | 5.04-5.05 | 2.16-2.17 | 5.47-5.48 | 28 | 8.25 |
| 70 | 13.75 | 6'4" | 5.06-5.08 | 2.18-2.19 | 5.49-5.50 | 27 | 8 |
| 67.5 | 13.5 | 6'2" | 5.09-5.11 | 2.20-2.21 | 5.51-5.52 | 26 | 7.75 |
| 5 | 7.25 | 3'1" | 6.03-6.04 | 2.78-2.79 | 6.04-6.05 | 1 | 1.5 |
| 2.5 | <7 | <3' | >6.05 | >2.80 | >6.06 | 0 | 1.25 |

FIG. 32

Male Age 16 Jawku Score & Percentile Rank

| Percentile Rank | Vertical Jump Inches | Broad Jump Inches | Pro-Agility Shuttle Seconds | 10-Yard Dash Seconds | 40 Yard Dash Seconds | Bench Press | Jawku Score |
|---|---|---|---|---|---|---|---|
| 99 | >30.75 | >9'2" | <4.25 | <1.67 | <4.75 | >38 | 10.75 |
| 95 | 30.5 | 9'1" | 4.26-4.27 | 1.68-1.69 | 4.76-4.77 | 37 | 10.5 |
| 92.5 | 30.25 | 9' | 4.28-4.29 | 1.70-1.71 | 4.78-4.79 | 36 | 10.25 |
| 90 | 30 | 8'10" | 4.30-4.31 | 1.72-1.73 | 4.80-4.81 | 35 | 10 |
| 87.5 | 29.75 | 8'8" | 4.32-4.33 | 1.74-1.75 | 4.82-4.83 | 34 | 9.75 |
| 85 | 29.5 | 8'6" | 4.34-4.35 | 1.76-1.77 | 4.84-4.85 | 33 | 9.5 |
| 82.5 | 29.25 | 8'4" | 4.36-4.37 | 1.78-1.79 | 4.86-4.87 | 32 | 9.25 |
| 80 | 29 | 8'2" | 4.38-4.39 | 1.80-1.81 | 4.88-4.89 | 31 | 9 |
| 77.5 | 28.75 | 8' | 4.40-4.41 | 1.82-1.83 | 4.90-4.91 | 30 | 8.75 |
| 75 | 28.5 | 7'10" | 4.42-4.43 | 1.84-1.85 | 4.92-4.93 | 29 | 8.5 |
| 72.5 | 28.25 | 7'9" | 4.44-4.45 | 1.86-1.87 | 4.94-4.95 | 28 | 8.25 |
| 70 | 28 | 7'8" | 4.46-4.48 | 1.88-1.89 | 4.96-4.97 | 27 | 8 |
| 67.5 | 27.75 | 7'7" | 4.49-4.51 | 1.90-1.91 | 4.98-4.99 | 26 | 7.75 |
| 5 | 18 | 3'8" | 5.33-5.34 | 2.41-2.42 | 5.55-5.56 | 1 | 1.5 |
| 2.5 | <17.75 | <3'6" | >5.35 | >2.43 | >5.57 | 0 | 1.25 |

FIG. 33

BIOMETRIC DATA GATHERING

CROSS-REFERENCE TO RELATED APPLICATION/INCORPORRATED BY REFERENCE

This is a division of and claims priority to co-pending U.S. patent application Ser. No. 14/121,226 filed Aug. 14, 2014 which makes reference to, claims priority to, and claims the benefit of U.S. Provisional Applications Ser. No. 61/959,476, filed Aug. 26, 2013 and Ser. No. 61/995,072 filed Apr. 3, 2014 with both entitled "Biometric Data Gathering".

The above stated applications are hereby incorporated by reference in their entirety.

FIELD OF THE INVENTION

The present invention relates to the measurement of human biometric data generated by physical activity using a unique universal motion exercising sensor module using a 6-DOF sensor of the mems type developed by JAWKU, LLC, a Delaware Company.

BACKGROUND OF THE INVENTION

Prior art devices for measuring physical exertion parameters exist, but have several drawbacks concerning the amount, type and quality of the useful data generated. For example, the range of forms of tracking and performance are limited. Sensors such as the NIKE FUEL BAND®, FITBIT ONE®, FITBIT FLEX®, JAWBONE UP®, and 24 HOUR FITNESS's BODYBUGG® are limited as essentially glorified accelerometers that only tracks steps taken, distance traveled, calories burned, and in some cases sleep activity. Sports activity and health sensors include wearable body sensors such as wrist watch sensors, as for example the Suunto Ambit2 S White, developed by a Finnish company for skiers, ear mounted sensors, and sensors incorporated in body clothing such as socks. Several bra sensors have also been developed such as the Tennis Performance Bra incorporating a miCoach heart rate sensor to track heart rate and calorie burn. The Basis fitness tracker bracelet works on a combination of a 3-axis accelerometer, a perspiration monitor and a skin temperature sensor to track beats per minute (bpm) heart rate patterns, steps taken and calories burned. Microsoft Inc. has recently developed a nerve bra sensor used to detect a change in nervous condition which may signal the onset of urges (such as binge eating).

BRIEF SUMMARY OF THE INVENTION

The improved sensing technology of the JAWKU™ sensor module tracks steps taken and calories burned like the prior art sensors above referred to and more. The universal 6-DOF sensor module interfaces with proprietary algorithms and preselected human motion parameters which enable an exerciser to be able to track human motions. This sensor module, for example, enables the user to run a sprint indoors or outdoors and then compare the user's time to that of top athletes who did the same sprint distance to see how the user compares, or compare the user's time to that achieved by the user's friends. The sensor module enables real time analysis and upload of biometric data during a user's activity or workout via pairing with the low energy Bluetooth system present in smartphones.

Further, all the biometric data can be saved on a built-in internal memory chip. This chip incorporates a compiler cpu made integral with the universal motion exercising sensor module (also referred to as the sensor module). This module is mounted on the human body by a wrist band, the combination module and wrist band referred to as a FITBANDT™ sensor wrist/ankle band. The user has the option to upload the data collected by the compiler using the Bluetooth capabilities of a smartphone or using a mini-USB cable link connected with the user's computer. This allows users the option to have their smartphone with them while they are exercising or the freedom to only have the sensor module with the internal memory chip with them during their training session. The chip data can then be uploaded at a time of the user's choosing. The sensor module wirelessly communicates with the Bluetooth® enabled smartphone which has an enabling app for either viewing the exercise data in a refined form on the smartphone's display screen or uploading the data to the user's home computer or to a remote cloud based computer system of a social fitness website the user has joined.

Optionally, the user may use the smartphone with the above referred to app installed in conjunction with a miniature wearable eyeglass viewing display (not shown) such as the one recently developed by Google, Inc. and marketed as the Google Glass® headset. The user can thus free up the smartphone display screen for other inputs while seeing the biometric data on the eyeglass miniature screen.

The sensor module gathers an immense amount of information and detailed feedback, as the user not only can wear the module during the user's workout but also all day to track things such as calories burned, steps taken, distance traveled, and activity level. The sensor module allows the user to track:
  Reps (each individual rep during exercise)
  Sets (each set that is done per exercise)
  40 yard dash (10 yrd, 20 yrd, 30 yrd, 40 yrd increments)
  100 yard dash
  Vertical jump
  Horizontal/broad jump
  Short/20 yard shuttle
  RAST (Repeated Anaerobic Sprint Test)
  Calories burned
  Steps taken
  Distance traveled
  Provides instant and real time analyses with the application
  Velocity
  Acceleration.

With the combination heart rate monitor/sensor module mounted by a chest strap or other suitable attaching devices well known in the art, the JAWKU FITBAND product can track heart rate/beat for a cardio assessment in addition to collecting pace and cadence data generated by the running activity of the user.

Various advantages, aspects and novel features of the present invention, as well as details of illustrated embodiments thereof, will be more fully understood from the following description and drawings.

BRIEF DESCRIPTION OF SEVERAL VIEWS OF THE DRAWINGS

Further features and advantages of the present invention will be apparent upon consideration of the following detailed description of the present invention, taken in conjunction with the following drawings, in which like reference numerals refer to like parts, and in which:

FIG. 3 shows in detail a top view of another embodiment of a sensor module cradle in which the sensor module of FIG. 1 may be gripped.

FIG. 3A is a cross sectional view of the cradle of FIG. 3 taken along section A-A.

FIG. 4 shows a detailed bottom view of the cradle of FIG. 3.

FIG. 5 is a perspective view of the universal sensor module for fitting in the cradles of the embodiments of FIGS. 1 and 3.

FIG. 7 is a fitness website STEP 1 sign up page.

FIG. 9 is a fitness website STEP 3 sign up profile and mode of training selection page.

FIG. 10 is a fitness website STEP 4 sign up, select membership level, type payment and product order selection page.

FIG. 14 is a fitness website page showing individualized user live progress history made towards a predetermined day's goal of exercise sets, reps per set and weights for a bench press workout.

FIG. 15 is a daily fitness website exercise summary page of a particular workout completed, such as the bench press exercise of FIG. 14.

FIG. 17 is a fitness website page a user selects to change a bench press exercise in terms of new heavier weights to be lifted and number of reps.

FIG. 18 is a fitness website page a user views to track the user's level of achievement compared to athletic fitness Combine goals for measuring athletic performance in the 40 yard dash, vertical jump, horizontal/broad jump and bench press.

FIG. 22 is a fitness website page the user accesses for particular information about a bench press workout contained in the FIGS. 21A and 21B podcast video library.

FIG. 24 depicts fitness website page the user accesses to view the user's current best scores in Sport Scouting Combine exercises.

FIG. 28 is a fitness website page showing a table used to establish Peak Power assessment.

FIG. 29 is a fitness website page showing a user selected Body Builder suggested weight table.

FIG. 30 is a fitness website page showing a blank summary page used to record user achieved number of reps and weights lifted for certain Bench Press exercises with app equation calculated 1 Rep Max and 1 Rep Max Unload weights.

FIG. 31 is the FIG. 30 website page showing reps completed and the user inputted lbs. lifted and the corresponding app calculated 1 Rep. Max and 1 Rep Max Unloaded weights.

FIG. 32 is a partial table showing the results achieved by males 12 years of age for six different American/Canadian football exercises with an overall percentile ranking achieved based on a proprietary "Jawku Score" algorithm for each exercise.

FIG. 33 is a partial table showing the results achieved by males 16 years of age for six different American/Canadian football exercises with an overall percentile ranking achieved based on the proprietary "Jawku Score" algorithm for each exercise.

DETAILED DESCRIPTION OF THE INVENTION

The invention relates to a state of the art sensor that is universal and has three human body location wearable applications. A tremendous advantage in economy is gained though the design of a universal motion exercising sensor module which is interchangeable to facilitate the sensor module being able to be easily and quickly taken out of each apparatus forming the each apparatus forming the above referred to human body location wearable applications and placed into the next for various forms of tracking exercise performance. This allows for the customization of holding devices for the sensor module and bands worn on the body or exercise equipment.

Figure 1:
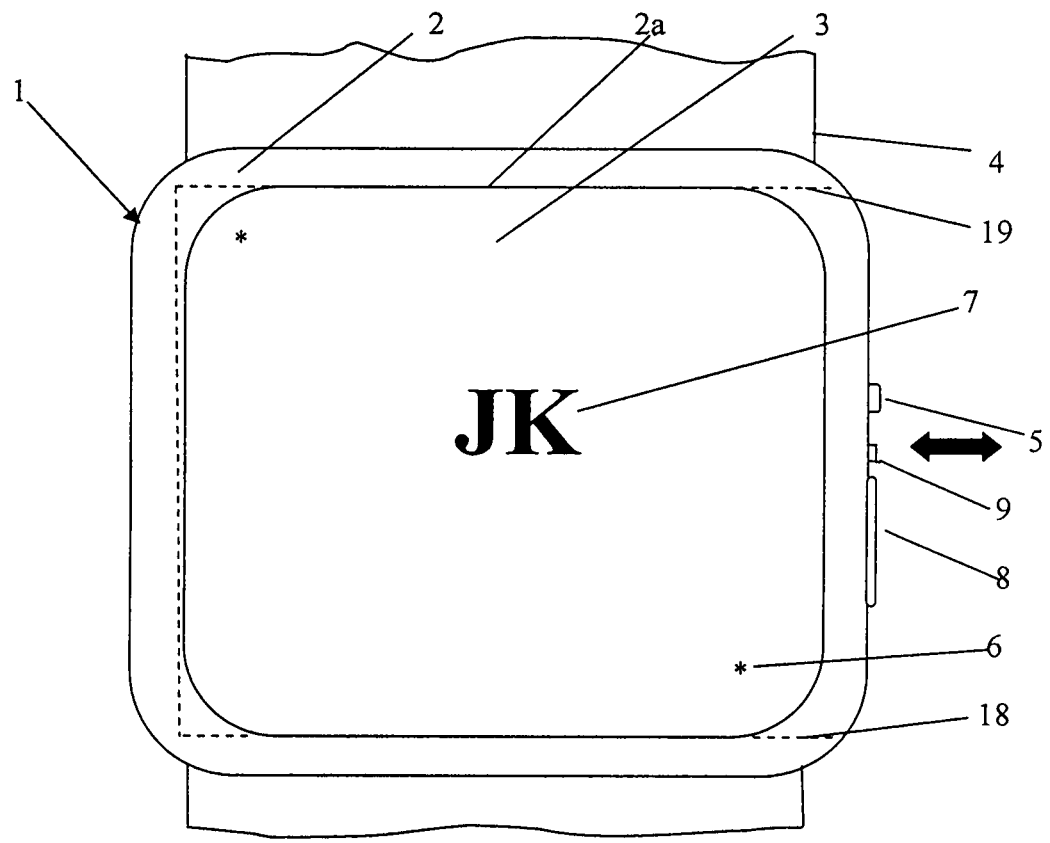
FIG. 1 is a top view of a first embodiment of the Fitband™ having a universal motion exercising sensor module mounted in a sideways loaded cradle embodiment attached to a wrist band.

A wrist Fitband™ 1 is shown in the FIG. 1 embodiment. The band portion 4 is made out of the highest quality non-allergenic silicon polymer (polysiloxane) sometimes referred to as silicone rubber as is known in the art of bracelet manufacture. Other materials well known in the art may be substituted such as 3-D printable acrylic or laser sintered nylon. The sensor module 3 (shown by itself in FIG. 5) is slipped horizontally (as shown by the double arrow viewed in FIG. 1) from right to left into a sensor module cradle 2. The cradle 2 has a side right port or slot opening with internal sidewalls 18-19 joined by a rear wall. The sensor module cradle 2 forms an integral part of the band portion 4. The wrist band portion 4 is adjustable to ensure correct body contact tightness for the tracking of accurate and precise motion data. The top surface material of the module 3 is normally an opaque blank. A power button 5 may be activated to allow one or more tiny low power consumption led lights 6 (shown in opposite corners) to be activated to display an alphanumeric symbol, name or logo 7 of the manufacturer shown as a JK for Jawku. These led lights are beneath the top surface of the sensor module and are positioned via small mirrors not shown) so as to illuminate the JK. The alphanumeric symbol 7 may also be illuminated by flashing the led lights 6 to call attention to the wrist band as an advertising or eye catching style detail. One of the led lights may also be used to flash a low power level alert for a lithium-ion polymer battery which powers the sensor module. The cradle 2 has an open rounded rectangular face 2a which overlays like a window frame the top of the module 3 as viewed FIG. 1 for viewing the logo 7 and led lights 6. Optionally, a basic chronometer time function may also be displayed in the plane of the logo 7. Market research has shown consumers prefer a multi-task watch wrist band to having to choose between a wearing a wrist watch and just a motion fitness wristband.

Figure 2:
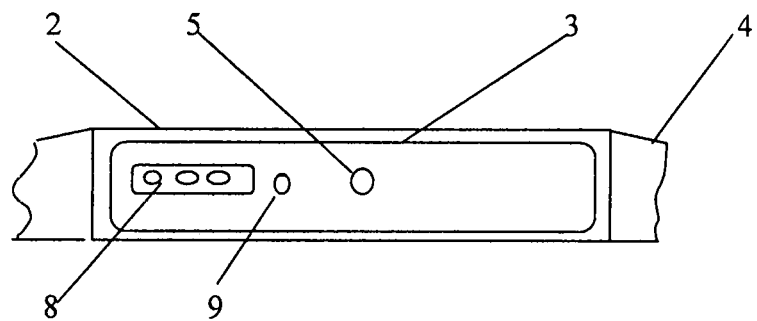
FIG. 2 is a right hand side view of the Fitband™ of FIG. 1.

FIG. 2 shows a side view of the sensor module 3 gripped in place by the cradle 2's sidewalls 18 and 19. On one side of the sensor module 3 is the power button 5 next to mini-USB port 8 for connecting with a USB data transfer link should the user wish to upload raw biometric data directly to a personal computer. Optionally, a recharging port 9 is shown located along side the port 8 for connecting a battery charger to recharge a mini-button style lithium-ion battery used to power the led lights and the universal motion exercising sensor module 3.

Figures 1A, 1B:
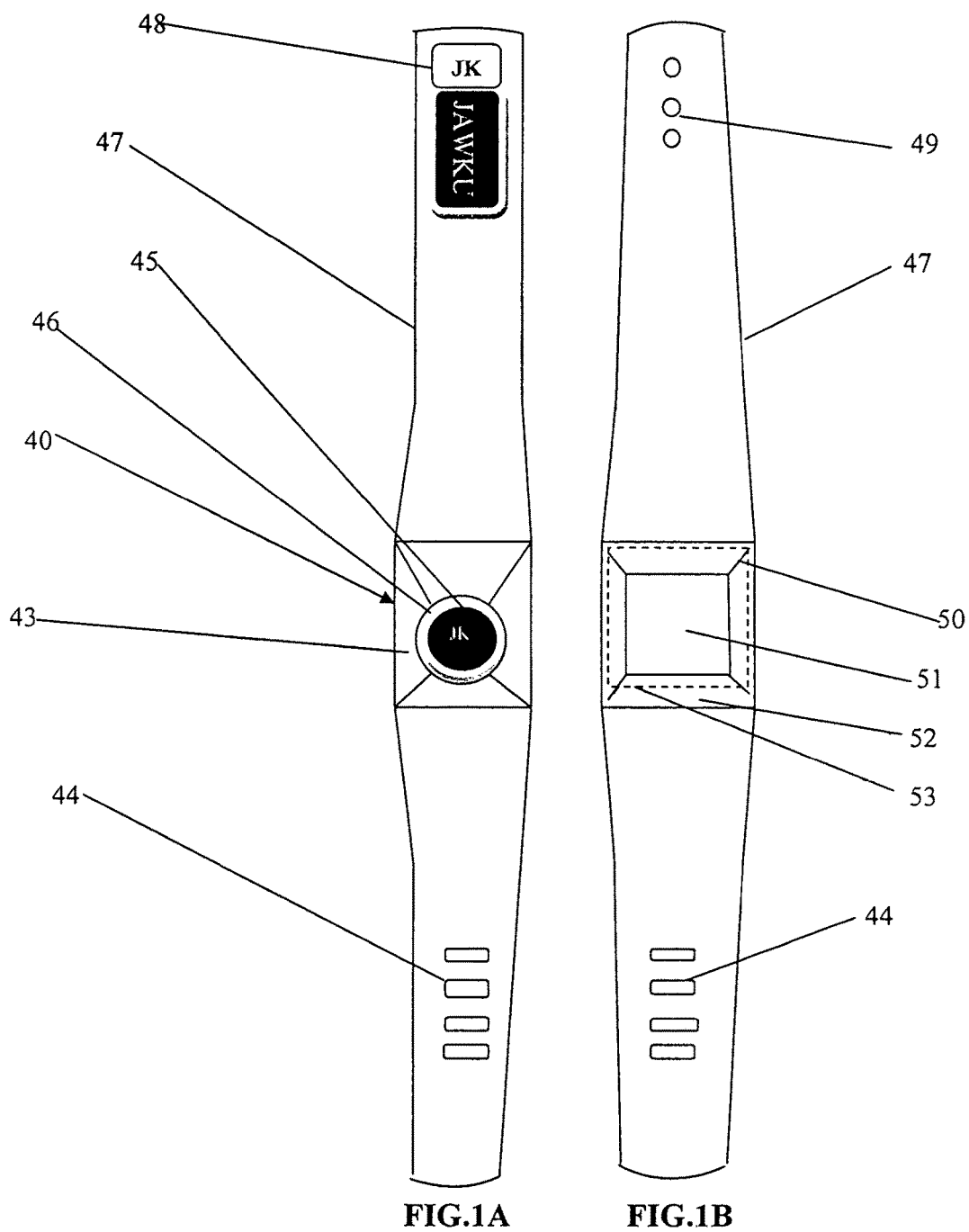
FIG. 1A is a top view of a second embodiment of the Fitband™ having the sensor module mounted in a bottom loaded cradle embodiment attached to a wrist band.
FIG. 1B is a bottom view of the embodiment of FIG. 1A.
Figure 1C:
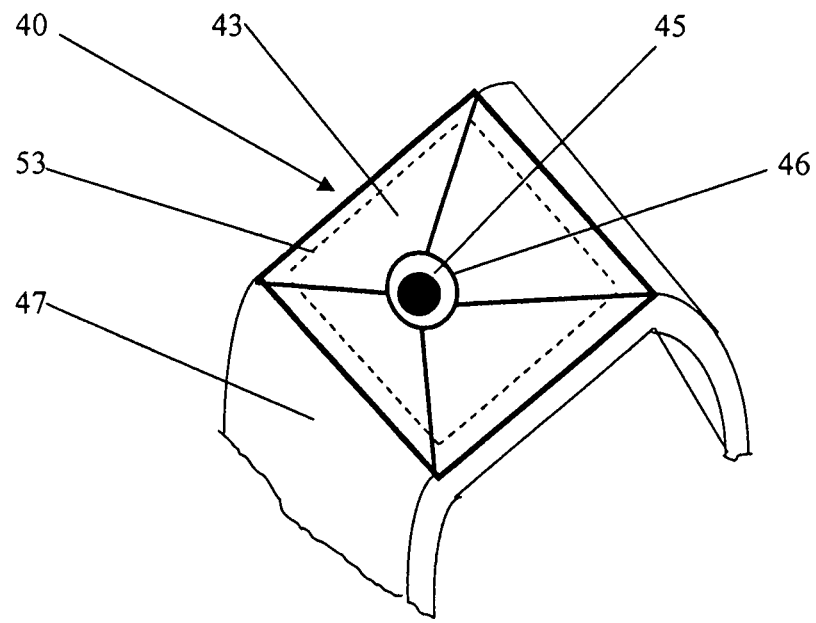
FIG. 1C is a perspective partial view of the embodiment of FIG. 1A.
Figure 1D:
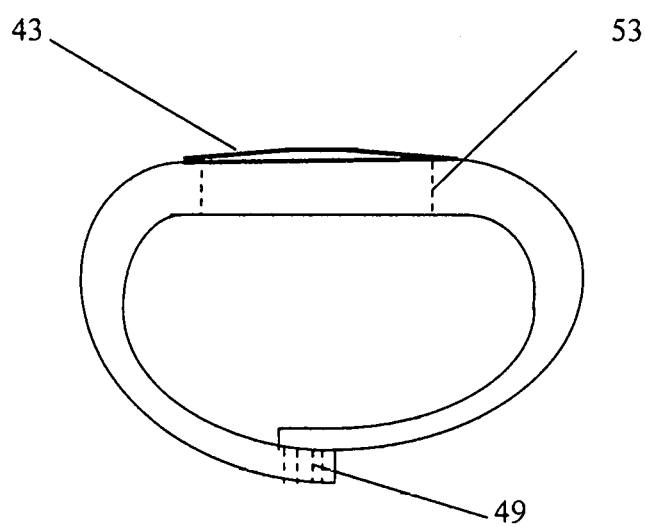
FIG. 1D is a side view of the embodiment of FIG. 1A with the wrist band closed.

A second embodiment of a wrist Fitband™ 40 is depicted in FIGS. 1A-1D. A universal sensor module 53 (shown in FIG. 1B in dashed hidden view outline form) similar or identical in shape to module 3 is slipped into a receiving square cavity opening on the underside of the wrist Fitband™ 40. Four flexible silicone walls 52 (shown in FIG. 1B) form the square perimeter of the cavity and function as flaps overlapping the bottom 51 of the sensor module 53 when placed in the cavity. Diagonal slits 50 separate the four walls 52 to permit the four walls to flex independently during insertion and removal of the sensor module 53. A flexible membrane power button 45 is located at the top of the sensor module 53 in place of the side power button 5 of the FIG. 1 embodiment. A wrist band portion 47 mounts an asymmetrical truncated very shallow four sided open top pyramid 43 (best viewed in FIG. 1C) having an opening 46 at the top to provide easy user finger access to membrane button 45. The pyramid provides a cover for the top of the sensor module 53. One end of the wrist band portion 47 on the bottom side has securing pegs 49 for snap fitting in slots 44 cut in the other end of the wrist band portion as shown in FIG. 1D. A logo 48 may be printed, debossed/embossed, or otherwise formed by or a combination of lettering techniques on the front side of the end of the wrist band portion 47.

Figure 1E:
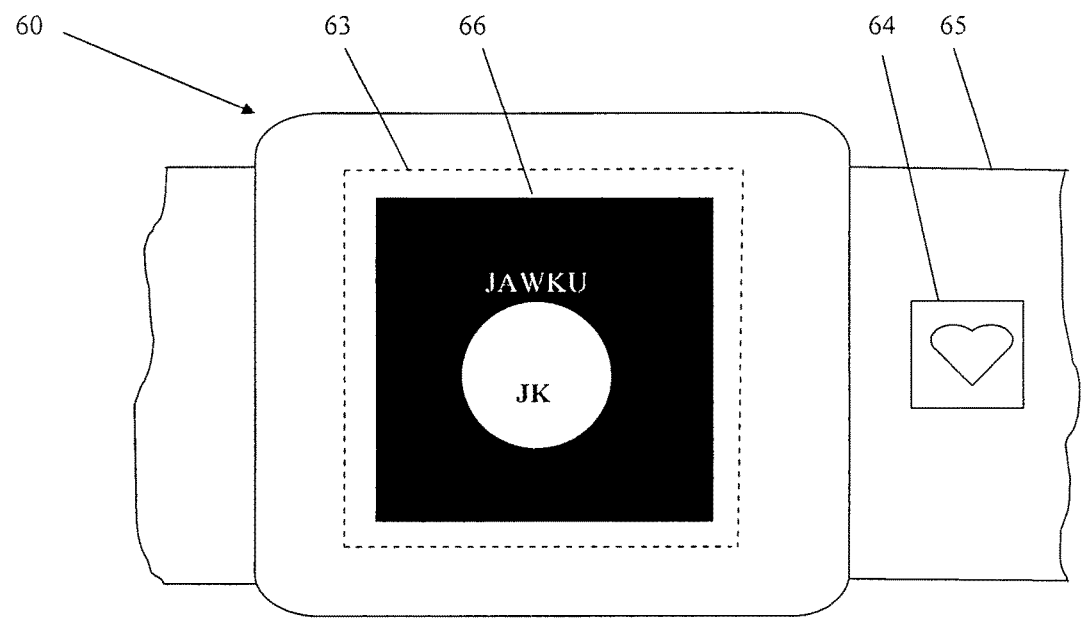
FIG. 1E is a plan view of a chest mounted Fitband™ having a sensor module permanently mounted to pair with a heart sensor on a chest band.

An embodiment of a chest Fitband™ 60 is depicted in FIG. 1E in a top view of a universal sensor module 63 (in dashed outline) combined with a heart sensor 64 mounted on a chest strap 65. The top of module 63 has a black portion 66 to indicate it is exposed for viewing. The white center circular area of portion 66 depicts a flexible power button membrane similar to membrane button 45. In this embodiment the module 63 is permanently affixed to chest strap 65 and not switchable with the other previously disclosed mounting cradles. For purposes of rapid shifting from, for example, arm weight lifting to leg weight training, a 6-DOF sensor can be individually permanently mounted on each of a wrist, ankle and body core strap.

Figure 1F:
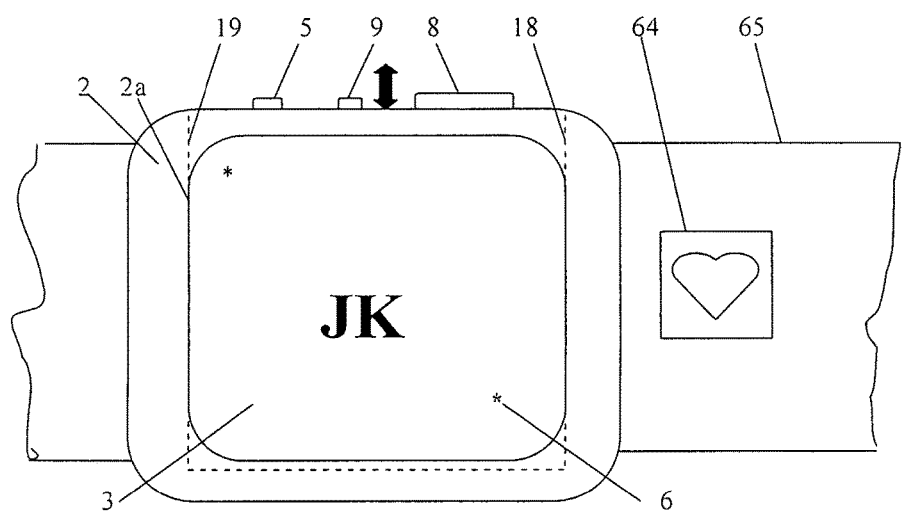
FIG. 1F is a top view of a chest mounted Fitband™ having the sensor module of FIG. 1.

Alternatively, the wrist universal motion exercising sensor module 3 may be used with a heart sensor 64 with both mounted on a chest strap 65. As shown in by the double arrow in FIG. 1F the module 3 is slipped into loading cradle 2 from the top when worn rather than the side loading direction of the FIG. 1 embodiment.

Alternatively, in another chest strap embodiment (not shown), the wrist universal sensor module 53 may also be used with a heart sensor mounted on a chest strap. The universal module 53 is placed into and removed from a rear loading cavity similar to the FIG. 1B embodiment and is held in place with the flexible flap wall 52 feature of FIG. 1B. The front of the module 53 is covered by the four sided open top pyramid 43 of FIG. 1A.

Optionally, it may be desirable to mount the heart sensor 64 on a separate chest strap. Module 53 has a mini-USB port and a recharging port the same as module 3 but must be removed from the wrist or chest band to permit access to the ports.

A special embodiment of the sensor module cradle is depicted in FIGS. 3, 3A and 4. This embodiment of the cradle 10 is designed to allow the cradle and movement sensor modules 3, 53 therein to be magnetically mounted on exercise equipment such as metal weight lifting equipment, e.g. bar bells. The universal sensor module 3 is slid into a plastic holding cradle 10 between two biased gripping walls 11, 12 located on each side of a base 15 which walls extend upwardly there from and are curved to extend over the top side edges of the universal sensor module 3. The curvature is designed to exert a downward biasing force on the module 3 sufficient to hold the module 3 in place on the cradle yet yieldable to permit hand force to remove the module. A rear retainer arm 13 extends upwardly from the base 15 and serves to arrest the sliding motion occurring upon the user loading the sensor modules 3, 53 onto the cradle base 15. The base 15 has an entrance ramp 14 having several rows of slightly raised ridges opposite the arm 13 which ridges prevent unchecked sliding out of the sensor module 3. A magnet 16 is secured preferable centrally to the bottom face of the base 15 in a cavity of a rounded raised receiving annular wall 17 reinforced by several support braces 18. Several smaller magnets may also be used in place of the single central larger magnet 16. The number and size of the smaller magnets depend on the design shape or contour surface of the weight lifting equipment being used. The bottom face of the base 15 may be curved to fit over a portion of the cross sectional curvature of a lifting bar having adjustable removable weights at each end rather than having the cradle directly affixed to a particular weight or kettle weight. Cradle 10 has an open face for access to the top membrane button 45 of the module 53.

The universal motion exercising sensor module 3 has a shell formed of light weight but durable plastic. The dimensions of the module 3 are compact in form and approximately 1 and 3/16 inch square by 5/16 inch high. As shown in FIG. 5, the module 3 has along one side face the mini-USB port 8, the rechargeable battery port 9 and the power button 5. The design of the universal sensor modules 3 and 53 is considered a universal design as the modules can be interchanged with wrist, ankle or chest strap mounted cradles and cradle 10.

This interchangeability provides advantages of simplicity, design aesthetics and economical cost to the user by reduction in the number of sensor movement modules needed by the user for different exercises. Interchangeability allows ease of replacement of damaged sensor modules. The magnetic cradle 10 is also sized to receive the sensor module 53 of the FIG. 1B embodiment and does not need to have the sensor module 53 removed from the cradle 10 to access its mini-USB port.

The exercising data detected by the motion sensor modules 3, 53, and 63 are automatically transmitted to a Bluetooth® enabled smart device, such as a smartphone having an app for refining the data and wirelessly transmit the refined data to a user's fitness website where automatic analysis of sensor data provides the user with ready access and digital storage of the data in easily understood form. Pairing a heart monitor with the invention's sensor module permits the user to self-track their fitness biometric data and goal exercise progress.

Figure 6:
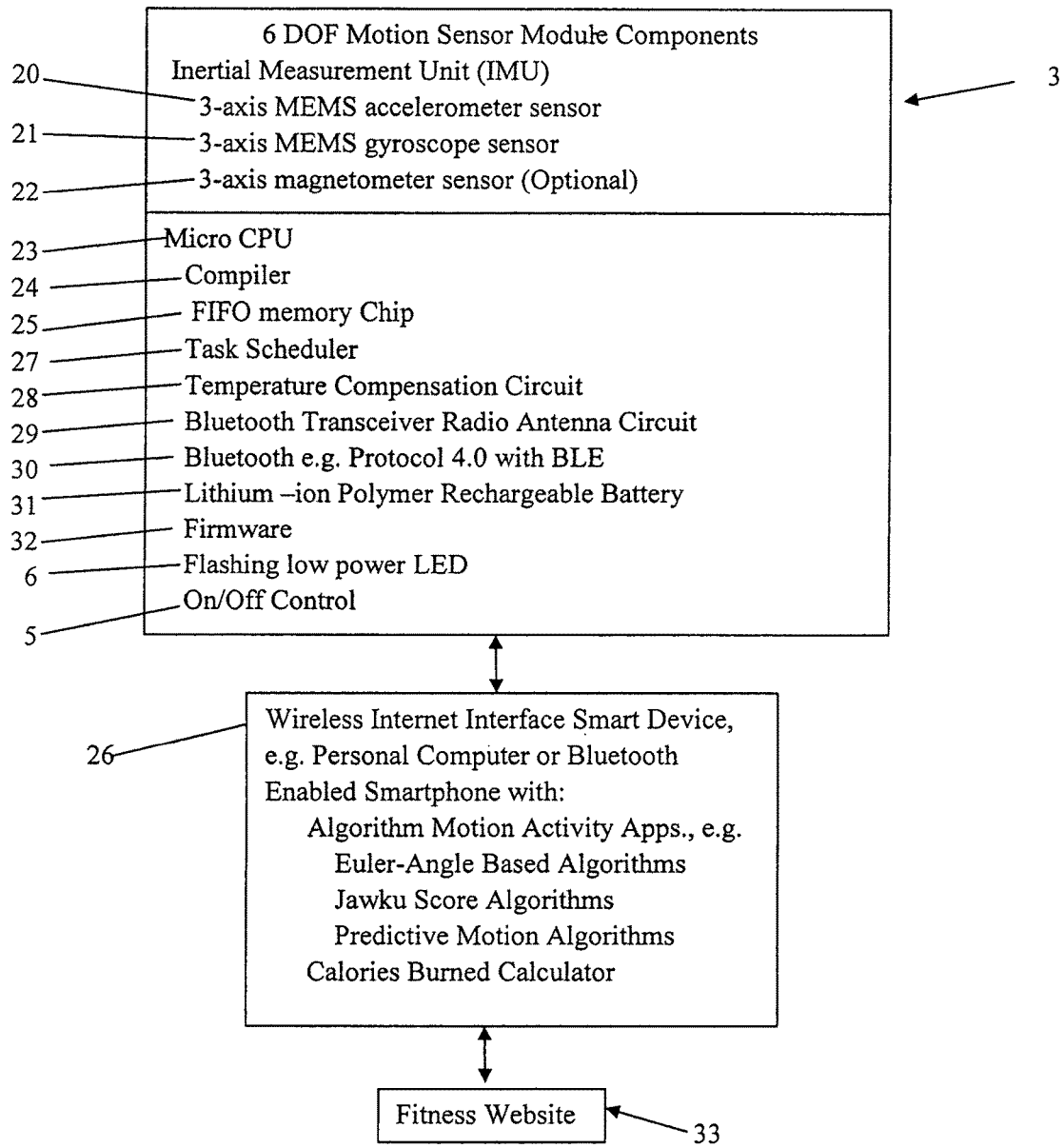
FIG. 6 is a block diagram of the main components of the biometric data gathering wireless communication system.

Components of the 6-DOF sensor inertial measurement unit common to sensor modules 3, 53 and 63 are depicted in FIG. 6 and include a tri-axial accelerometer 20 and a tri-axial gyroscope 21. Optionally, a tri-axial magnetometer 22 is added for a full 9-DOF sensor version for user location data through use of GPS waypoints. Power is provided by a lithium ion rechargeable battery 31 preferably in square button form and is controlled by the on/off button 5 or membrane button 45. Activation of these buttons by the user initiates the start of the exercise or tracking. The LED light 6 signals both the start of the exercise and also flashes to signal low battery life. A microprocessor 23 controls the sensor system's operation. The microprocessor can be of the DMP type (Digital Motion processor). The DMP provides six-axis motion fusion data in rotation matrix, quaternion, Euler angle or raw data format as inputs for the six degrees motion algorithms used. The Euler angle format is suitable for use with either a single rotation order algorithm or an optimal rotation order algorithm which algorithms are downloaded from fitness website 33 as an app to the wireless interface of the smart device 26.

Other components include an integrated internal memory chip 25 of the FIFO type for motion biofeedback or motion logging. Integral with the memory chip is a compiler 24 used to control sensor data reception and to transmit the same in coded form suitable for the wireless internet interface of the smart device 26. Examples of the smart device 26 are Bluetooth enabled personal computers and Bluetooth enabled smartphones.

Integral with the microprocessor 23 is a task scheduler circuit 27 which among other tasks controls the order of data packet transmissions and timing of sleep mode to power down unused sensors. An embedded temperature sensor and circuit 28 is provided for calibration accuracy. The circuit 28 has an on-chip oscillator with as an example +/−1% variation over the operating temperature range and calibration circuitry.

A Bluetooth transceiver radio antenna and circuit 29 is integrated within the module for wireless transfer of data to a Bluetooth enabled smartphone. Bluetooth™ protocol 4.0 circuitry 30 is provided with BLE power consumption. A higher Bluetooth® protocol may also be used depending on the compiler coding.

As an alternative to a Bluetooth® protocol, other communication standards for wireless data transfer may be used such as 4G, WiFi and Zigbee®. Those skilled in the art will readily understand the need for other basic components such as those disclosed in U.S. Pat. No. 7,219,033, to Kolen, which disclosure is hereby incorporated in its entirety. Firmware 32 protects vibration shocks to the module and is an example of such other basic components.

The wrist Fitband™ 1 with mounted sensor module 3 tracks reps, sets, steps taken, velocity, acceleration, and other biometric motion data. Calories burned are accurately calculated knowing the above sensed biometric data. An ankle/leg Fitband™ which uses the universal sensor module 3 with a larger band size than the wrist band 4 is secured to a correct tightness when placed on the ankle/leg for measuring motions for various pushing, pulling, running and jumping activities. For comfort reasons, a silicone material is preferred for the band material.

In the embodiment of FIG. 3, the sensor module 3 is encased in the cradle 10 with the magnets 16 permitting secure and easy attachment on metal weights. The user may thus move the cradle 10 between typical metal exercise equipment found in a gym as the user progresses from one piece of equipment to another. Rare earth metals serving to act as magnets for the sensor module on gym equipment permit it to be attached, as examples, to free weights, weight stacks, cable machines, dumbbells and barbells. With this, the sensor module 3 tracks the user's reps, sets, calories burned, steps taken, velocity, acceleration, and more biometric data listed above. The weight pound sizes lifted are manually entered into a host smart device 26 or smartphone having an app page screen.

One alternative method to having the user go through a later step of entering (on the smartphone) the weight size information is to employ predictive type algorithms. These algorithms compare known expected physiological data results for a user's age group and physical conditioning rating for a given set of reps of different size weights with both the real time biometric data being generated and the known moving average personal history data of the user for the particular weight lifting exercise being monitored. The predictive algorithms can then infer which size weight is being lifted in real time, such as a 5, 10, 20 lb weight etc. As a user over time advances in conditioning strength the algorithm adjusts the moving average. This relieves the user of the time consuming task of having to accurately enter each weight size. The user has already been given a weight lifting routine which greatly simplifies this step. Additionally, although the lifting routine typically calls for a warm up order of increasing and then decreasing weight size being lifted, should the user digress and mix or skip a low end or a high end weight set, the data generated is interpreted by the predictive algorithm to automatically infer correctly the weight being lifted. The predictive algorithms are accurately best used when a personal data history has been developed and logged by the website.

Acceleration and velocity measuring proprietary algorithm programs are installed or downloaded to the Bluetooth® enabled smartphone. These apps wirelessly receive through the smartphone the motion data collected by the sensor module 3. The apps refine the raw data to send a useful and easily understood alert signal to the sensor module 3 in the event a correct threshold level for building muscle is not being maintained. This signal can be a particular flashing light color from one of the led lights 6 (other than the low battery power led light). In this manner, the user is alerted to at that time discontinue the exercise set as no longer being effective.

A proprietary cardio and weight lifting assessment (explained further) can be generated automatically using any of the universal sensor modules such as 3 or 53 mounted on any of the wrist band, the ankle band, the combination heart monitor sensor with chest strap and the magnetic cradle 10. This assessment is an important tool which assists in creating an individualized program for the user after they perform the specific motion/weight lifting tests set forth in the assessment protocol.

Optionally, the user may also elect to purchase a low energy Bluetooth® enabled or WiFi enabled weight scale to track body weight and body composition or body mass data that will be analyzed in real time by the assessment program. The data from the weight scale is automatically wirelessly sent to the smartphone of the user.

By use of state of the art technology and backend programming on the apps and the social website, the profile questions asked at the website signup of the user, and the cardio and weight lifting assessment data provided by the universal sensor module and heart rate monitor, customized fitness programs specific to each individual are developed to create the ultimate fitness and health-training tool.

These programs eliminate the need for and high cost of personalized trainers. The expense and time required to go to a professional gym can be avoided by the user in favor of the privacy and scheduling of exercise time for a home exercising program. Unnecessary waiting on others for limited gym equipment to become available is also avoided.

The user's smartphone downloaded with proprietary motion algorithm apps combined with the above state of the art motion sensing technology enhances a social website internet fitness training (SWIFT) based support system. The user is guided by unique personalized differentiators that guide physical training, provide feedback and analysis, giving the user a tool to better fitness and dietary health goal decisions.

Once the user downloads the just referred to smartphone app, the user is greeted with a very friendly and unique signup page. This page gathers information about the user to help generate and create an individualized workout program and profile based on the user's body type, fitness level, goals, and preferred mode of training.

Figure 8:
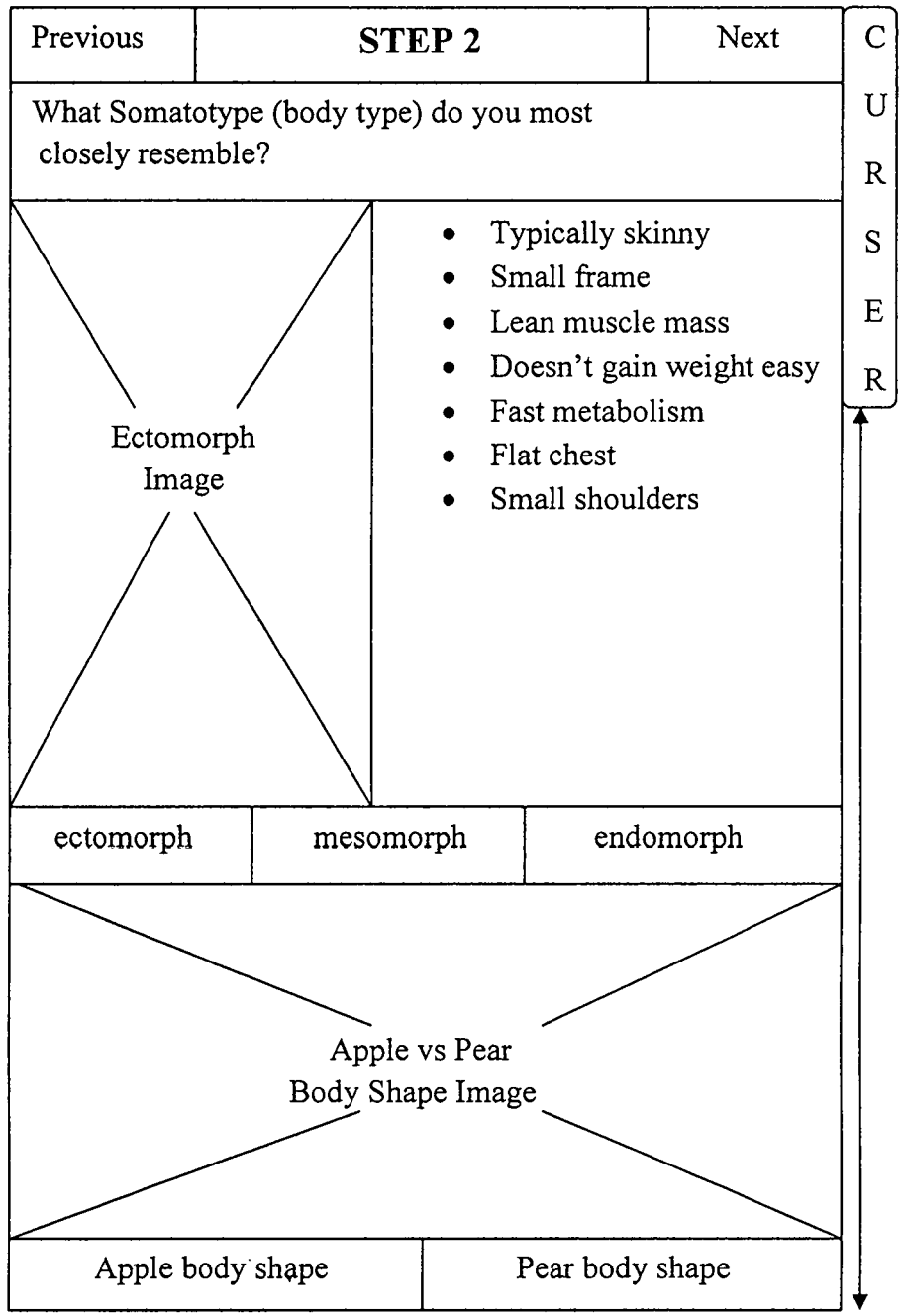
FIG. 8 is a fitness website STEP 2 sign up body profile page.

Upon accessing the Jawku website, the user in STEPS 1-2 enters personal profile information, such as name, gender, age, physical description parameters, fitness programs engaged in, if any, current diet programs and diet preferences, sports engaged in, etc. as shown by FIGS. 7-8 which depicts website pages capable of being viewed on a smartphone. The user is asked in STEP 2 to associate with a somato-type or body-type using photos and descriptions provided as shown by FIG. 8.

In STEP 3, as shown by FIG. 9 which depicts a website page capable of being viewed on a smartphone, the preferred training site, such as at home or a professional gym, indoor/outdoor is elicited from the user. The user is also asked to select from six modes of training:

1. Tactical (e.g. crossfit, military, run+gun) (high intensity interval training)
2. Athletic Performance (Sport agnostic, it does not matter what position played with goals being to get bigger, faster, stronger.)
3. Weight Loss (Moderate-low intensity for sedentary lifestyle)
4. Bodybuilding (e.g. increase muscle mass, decrease fat, targeted body sculpturing)
5. Health +Wellness (Healthy lifestyle)
6. Endurance Athlete (e.g. marathons, strong man competitions, tri-athlete, runners, swimmers, bikers, hikers, surfers, etc).

The STEP 3 web page also captures height, weight, age, athletic/nonathletic, and experience level, low/medium/high.

In STEP 4, the user accesses a web page shown by FIG. 10, wherein the user joins the website by signing up for a membership level, selects the type of payment, orders the sensor kit, and upon receiving the kit, conducts the cardio and weight lifting assessment exercises outlined in an instruction package and sends the biometric data thus gathered to the website.

Jawku website's intellectual property and proprietary programs including algorithms are utilized to develop a personalized training program unique to the user. The website evaluates the user's profile page and the cardio and weight lifting assessment data to recommend the weights the user should use during training in addition to other items for training and testing purposes. A weekly/monthly customized user schedule for weight exercises, ranges and reps and sets is generated. Progress targets when met cause these schedules to be regularly upgraded. Schedule changes are also made when target goals are not achieved.

Figure 11:
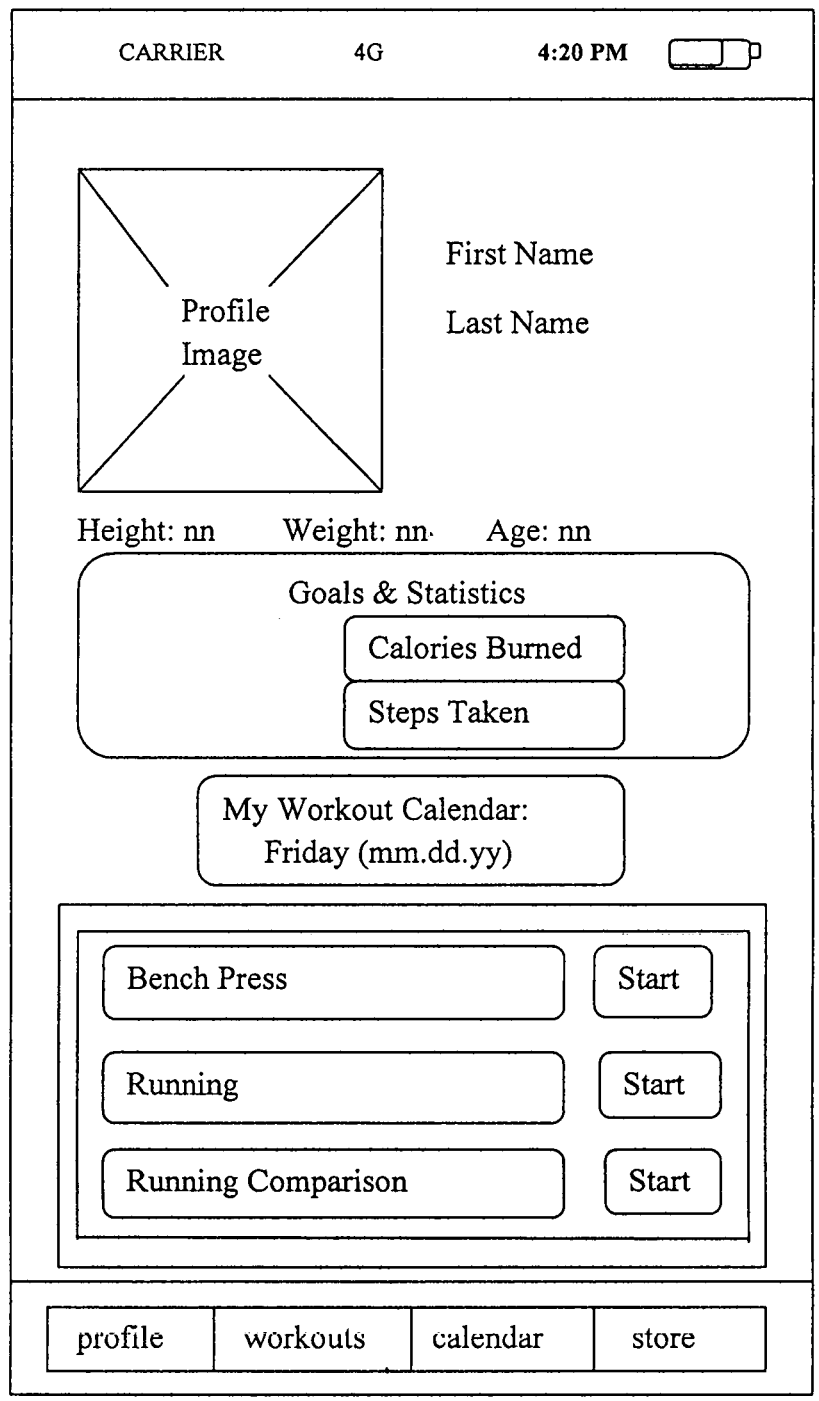
FIG. 11 is a fitness website user profile, workout calendar selection and exercise goal progress history page.

A profile page, as depicted by FIG. 11 which represents a website page capable of being viewed on a smartphone, shows goals and statistics of the user, such as calories burned and steps taken. The user can call up, using a workout calendar a particular day and particular exercises attempted, such as a bench press, running and comparison of goals set versus the exercise workout progress.

Figure 12:
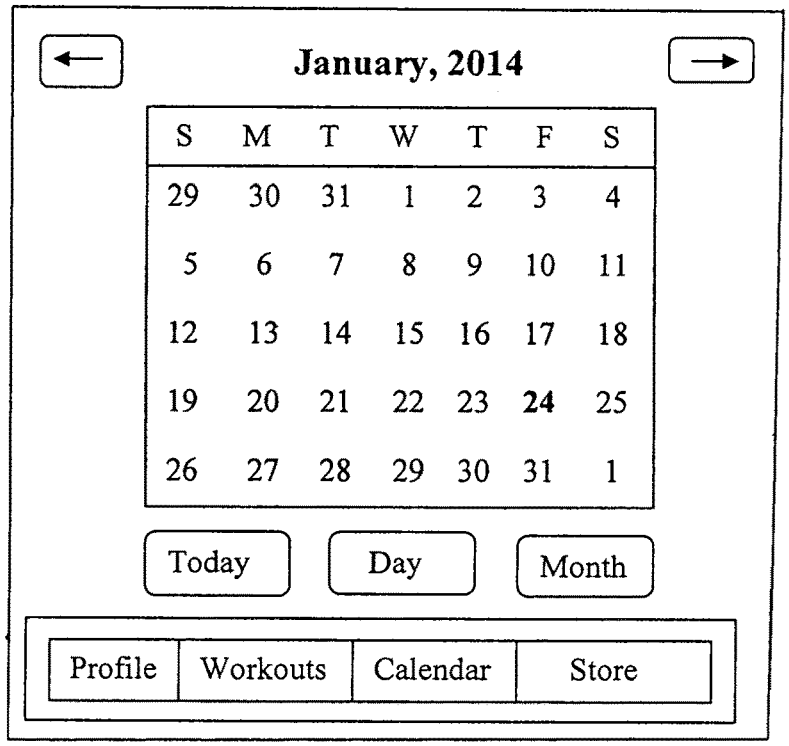
FIG. 12 is a fitness website individualized user calendar page with selection of particular day's workouts or weekly workouts or monthly workout schedule.

A daily, weekly or monthly workout calendar, as depicted by FIG. 12 which represents a website page capable of being viewed on a smartphone, shows Friday, the 24th of January 2014 highlighted as the user selected calendar date being reviewed to obtain the workout exercises scheduled for that day.

Figure 13:
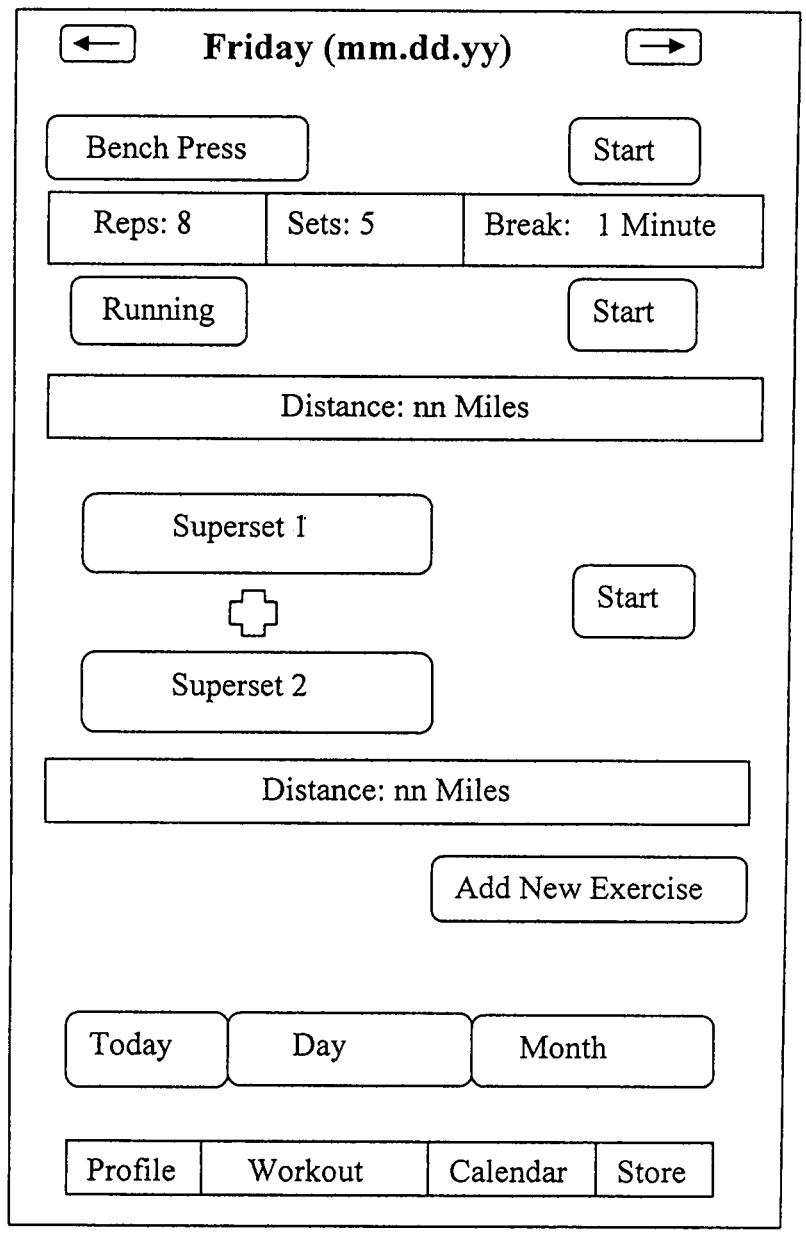
FIG. 13 is a fitness website individualized user workout template page setting forth the various types of strength and endurance exercises scheduled for the day in terms of bench press weights, reps and distance running goals with optional user selected additional new exercise and reps therefore.

A workout template, as depicted by FIG. 13 which represents a website page capable of being viewed on a smartphone, is a tool the user reviews before the start of a workout to see the overview of the workout or training scheduled with timed breaks for a particular day. When the user starts the workout, each exercise has a page like this that lists information about the exercise, the weight, sets, and reps they are supposed to perform including timed rest breaks. Cumulative "supersets" are also tracked. The user is given the flexibility to add new exercises besides the bench press and running exercises shown only by way of example.

A history analysis, as depicted by FIG. 14 which represents a website page capable of being viewed on a smartphone, is provided the user as each exercise is performed to show the live progress, history, and if the scheduled exercise (sets, weights, and reps) were all completed. This history information is stored in a memory profile at the fitness website.

In FIG. 15, a daily exercise summary of a completed scheduled exercise, such as a weight lifting bench press exercise of FIG. 14, is depicted in the form of a website page capable of being viewed by a smartphone. This summary is logged in to the history profile of the user and available for future reference. All types of exercises completed for that day are likewise logged into a user's history profile.

Figure 16:
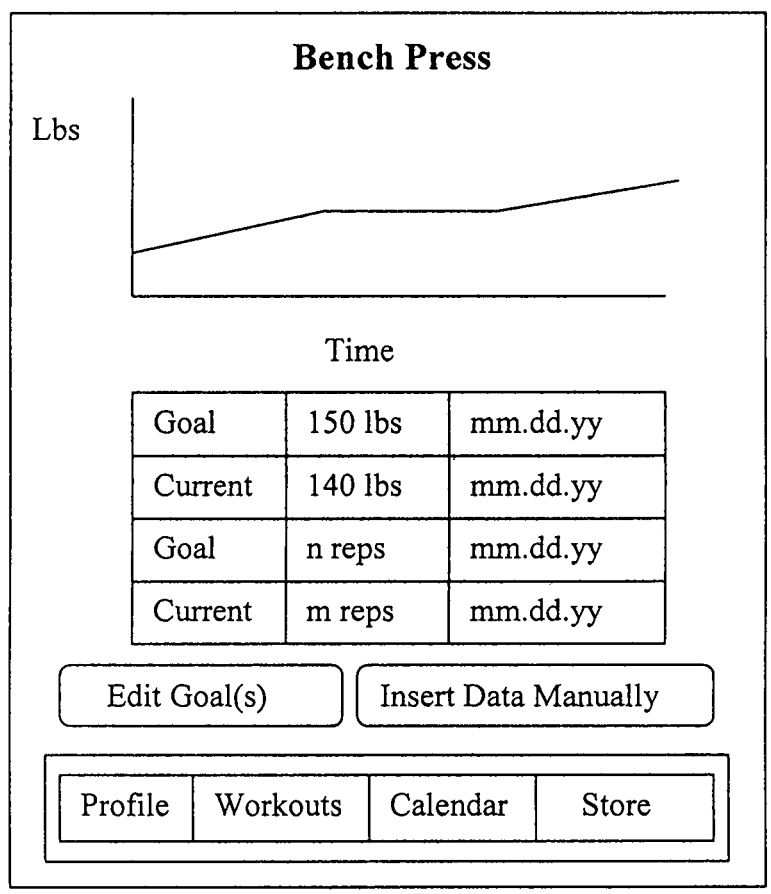
FIG. 16 is a daily fitness website graph of a user's particular scheduled workout showing pounds lifted over time and goals set against current weights lifted and reps completed.

A graph of a bench press exercise of pounds of weight lifted over time is depicted by FIG. 16 which represents a website page capable of being viewed on a smartphone. In the example shown, the user is provided with a comparison of the goal of 150 pounds to be lifted with the actual 140 pounds lifted along with a comparison of goal reps to the actual number of reps achieved. It is necessary for accuracy for the user to manually enter the actual weight being lifted via a computer or smartphone which in turn communicates this to the fitness website.

For the selected exercises or Sports Combine tests (as an example the NFL Scouting Combine tests), goals can be created and then tracked so the user can see as an incentive what effort is needed to reach and exceed user goals. A website page capable of being viewed on a smartphone is depicted in FIG. 17 for a bench press exercise. This page is provided for the user to create and enter the exercise weight being lifted with the reps automatically counted using the data from the 6-DOF sensor module.

Plural goals can be tracked on the same website page as shown in FIG. 18 for the 40 yard dash, vertical jump, horizontal/broad jump and bench press Goals which tests are currently employed by professional football combines such as the NFL Scouting Combine.

Figure 19:
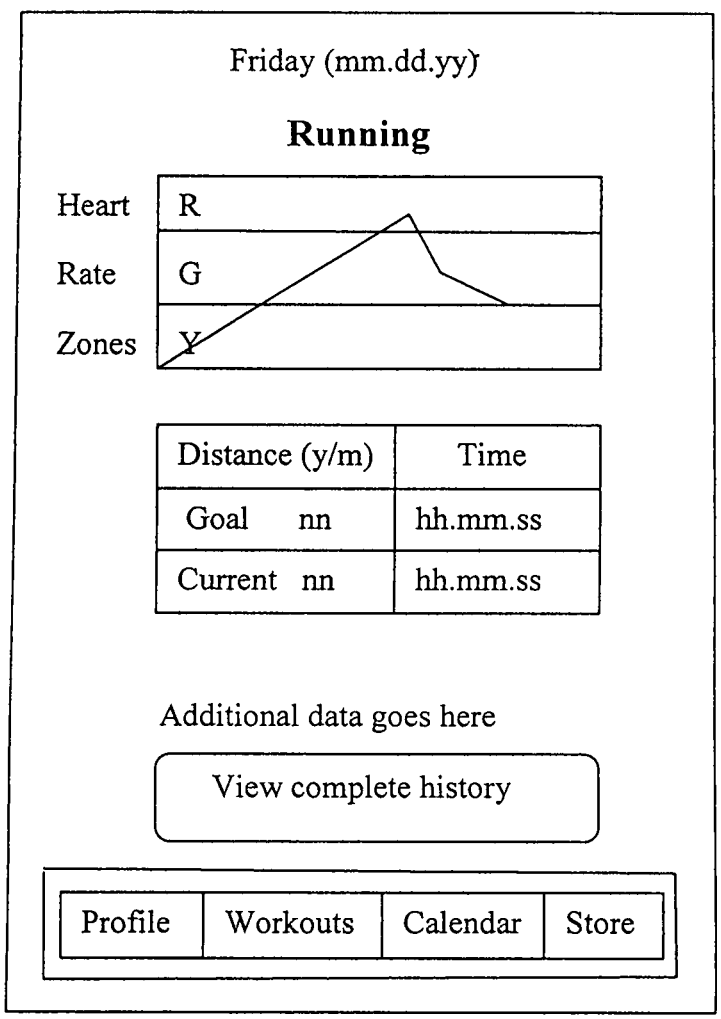
FIG. 19 is a fitness website page graph showing an individual user's heart rate time in high, medium and low exertion modes of endurance running training.

For various endurance exercises, such as running or distance training as for a marathon, the app monitoring the data given by any of the sensor modules 3, 53, 63 and the heart sensor produces data in graph form relevant to heart rate zones. A heart rate graph, as depicted by FIG. 19 which represents a website page capable of being viewed on a smartphone, in real time is provided. The top ⅓ of the graph represents the red zone of peak heart rate effort, the middle portion represents the green zone of normal heart rate effort, and the bottom ⅓ of the graph represents in yellow a warm up and cool down zone of lowest heart rate effort.

Figure 20:
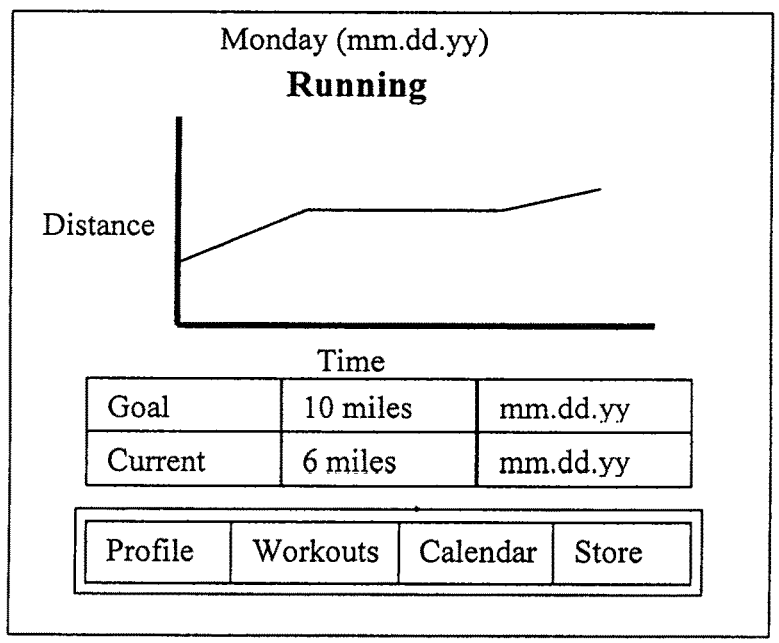
FIG. 20 is a fitness website page of an individualized daily live graph showing distance run over time comparing a distance running goal with the current distance pace.

As depicted in FIG. 20 which represents a website page capable of being viewed on a smartphone, running data is displayed in the form of a graph of distance over time, how it compares to the user selected goal, the current distance run and the user's running history. Similarly, other distance related exercises such as cycling and swimming can be displayed.

Figures 21A, 21B:
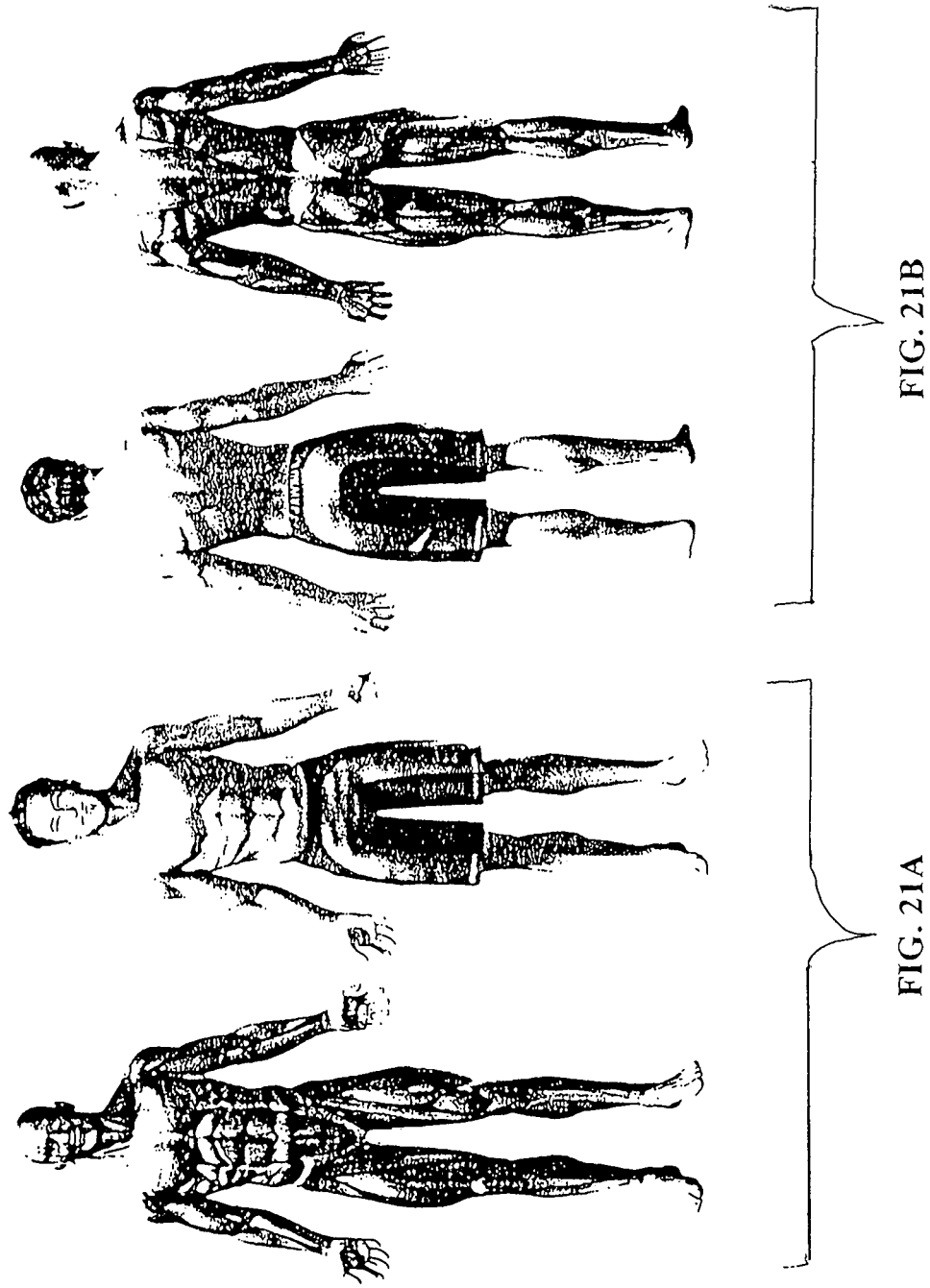
FIGS. 21A and 21B are frontal and rear views of a fitness website page of rotating avatar figures used to access a library of exercise podcast videos of particular muscle or muscle group workouts.

The website workout page, depicted in FIGS. 21A and 21B is capable of being viewed on a smartphone. Left FIG. 21A shows two avatar figures with one showing major muscles/muscle groups in some detail of a male image in a frontal view and the adjacent avatar showing the normal outward appearance. If the website user provides a facial photo and gives permission, the face on the avatar can be that of the user only for the user's website account.

Right FIG. 21B is a rotated rear view of the avatars of FIG. 21A. The avatar figure is referred to as an Imagetron™. Also, a female avatar version of the Imagetron™ can optionally be viewed called a Femtron™ (not shown). The avatar is caused to rotate to show specific muscle group locations. The avatar's purpose is to permit the user to understand and locate muscle groups to access a description of each muscle or muscle group. The user simply clicks on a specific muscle or muscle group area to gain access to filters allowing the user to explore Jawku's professional data base of over 500 exercise video podcasts with both audio and text instructions particularly helpful to blind or deaf users. The user may choose to view an enlarged area of the muscle group clicked on to see more detail such as the Latissimus Dorsi (Lat) back muscle.

Also, alphanumeric reference figures (not shown for simplicity) can be overlayed over the specific muscle or muscle groups of the avatar to allow the user to click on index library filters. These filters allow the users to explore Jawku's professional database of over 500 exercise videos.

The FIG. 22 website page is capable of being viewed on a smartphone. FIG. 22 is an example of a bench press page selected from the index library filters. This website page provides the description of each muscle or muscle group, a list of exercises that can be performed for each muscle based upon the user's workout profile and equipment needed. Descriptions of the exercises accompanied by a color video for each exercise with related audio and text instructions can also be select. Also provided on the FIG. 22 website page is a user button to add or substitute the example exercise with another exercise directly into the user's workout program.

Figure 23:
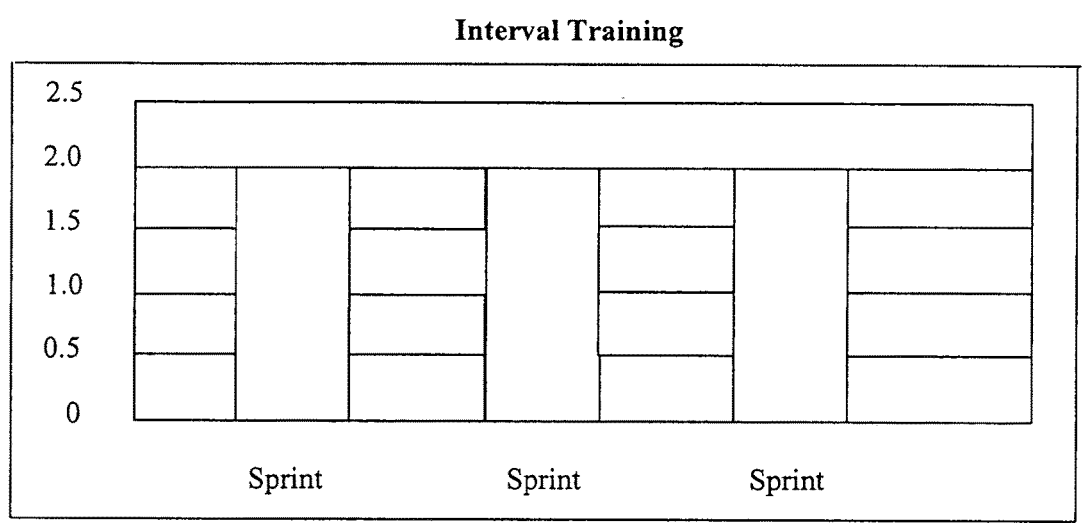
FIG. 23 depicts a fitness website page the user accesses to view interval training history.

In most repetitive exercises, it is common practice to provide rest intervals between each rep which require the exertion of large amounts of energy and places strain on the muscle groups and joints undergoing conditioning. The Jawku exercise website provides interval training charts for each such exercise to aid the athlete in proper rest time pacing in a proven safe, effective and time efficient manner rather than the far more aggressive sessions promoted on television, such as Insane Workout. FIG. 23 is an example of such a chart for interval sprint training. Note the time rest intervals increased from the first to the third sprint interval shown as the number of sprints increase to avoid joint injuries often caused by overtraining. These time intervals are based on the goals set forth for the user to reach. An overlay chart (not shown) can also be provided to allow comparison of optimum rest times versus actual rest times of the user.

Benefits of TRUE interval training are:
1) Develops all cardiovascular systems:
   A. Aerobic
   B. Anaerobic
   C. Peak-PC/Alactic (anaerobic system for gauging various exercise modes)
2) Burns Calories
3) Increased Motivation
4) Increased Cardio Strength
5) Increased Metabolism.

A wide variety of Sports Combines exist in which have developed specific athletic skill tests to measure where an athlete is ranked. Specific exercises and programs are developed to improve an athlete's performance in weak areas revealed by these tests. In American professional football, the NFL Scouting Combine uses these tests to evaluate prime candidates for the team drafts. The Jawku motion sensors above disclosed can measure at least six of these skill tests. A website page shown in FIG. 24 which is viewable on a smartphone measures an athlete's performance in the 40 yard dash, the bench press, the vertical jump, the proagility 5-10-5 (short 20 yard shuttle), the broad jump and the 3 cone drill/L-drill. A specific app loaded on the smartphone is used to display the web page.

J-Score

Figure 25:
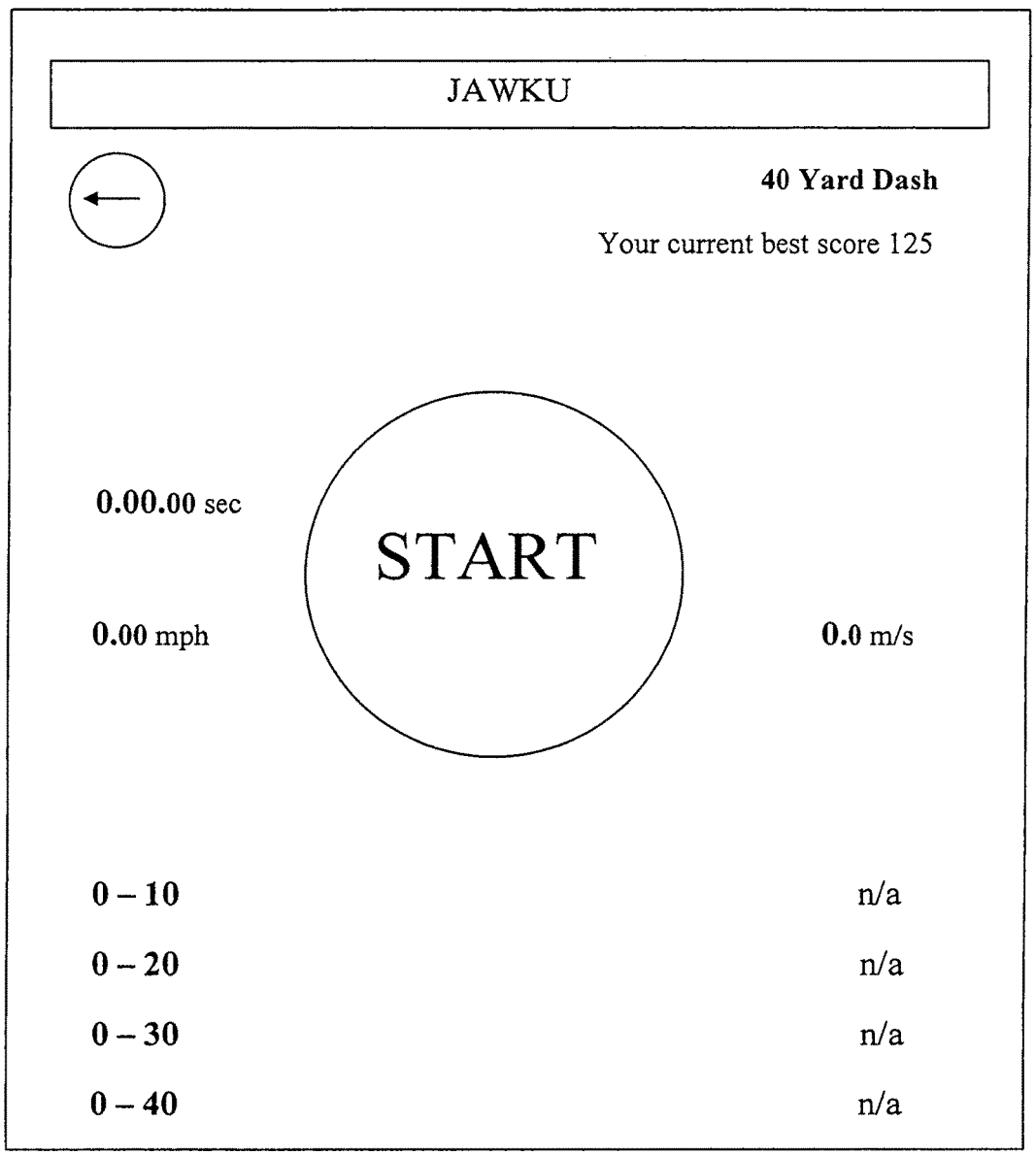
FIG. 25 depicts fitness website page the user accesses to start the measured time and velocity of a 40 yard dash Scouting Combine test.
Figure 26:
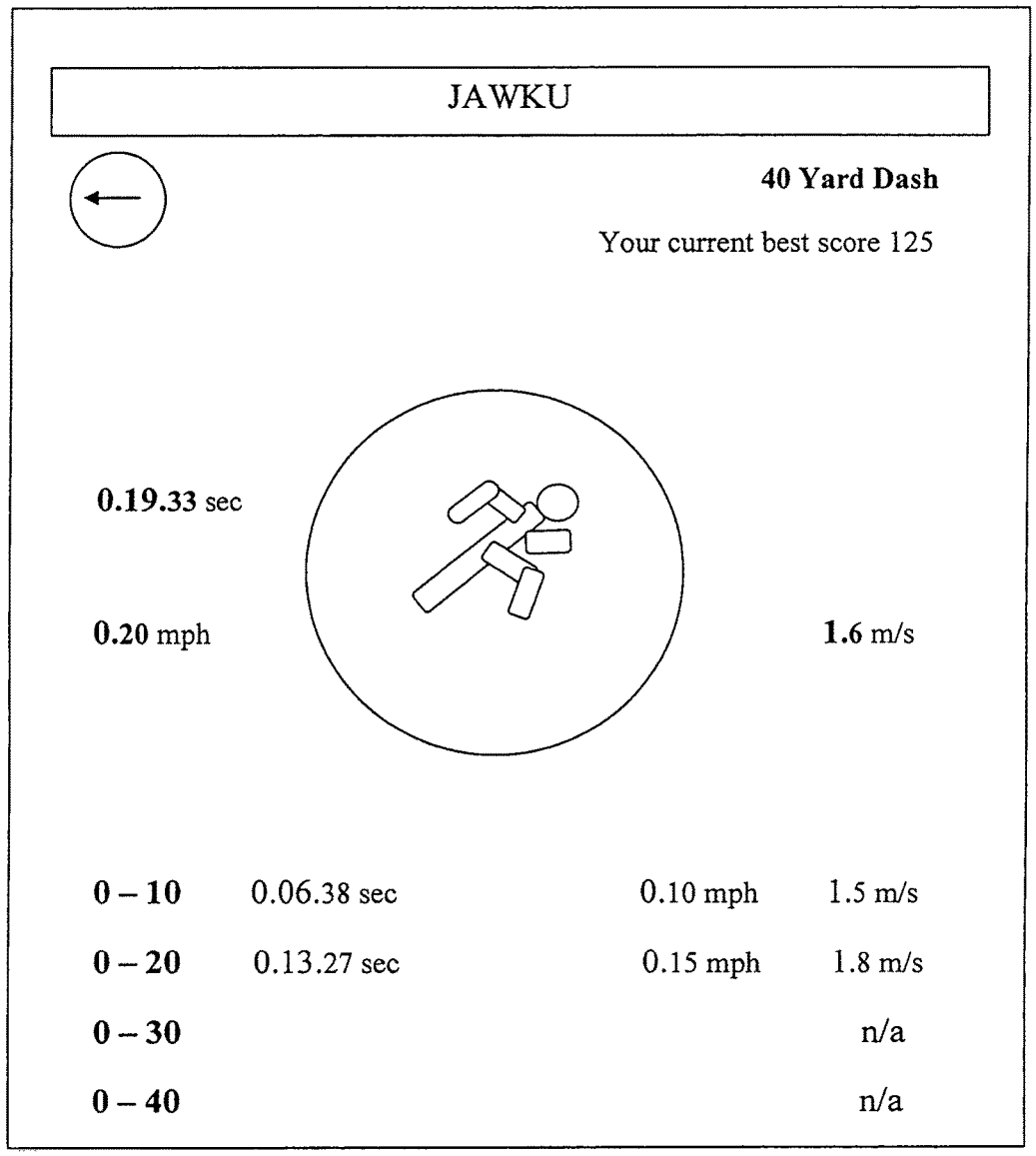
FIG. 26 is the FIG. 25 page showing progress made midway through the 40 yard dash.
Figure 27:
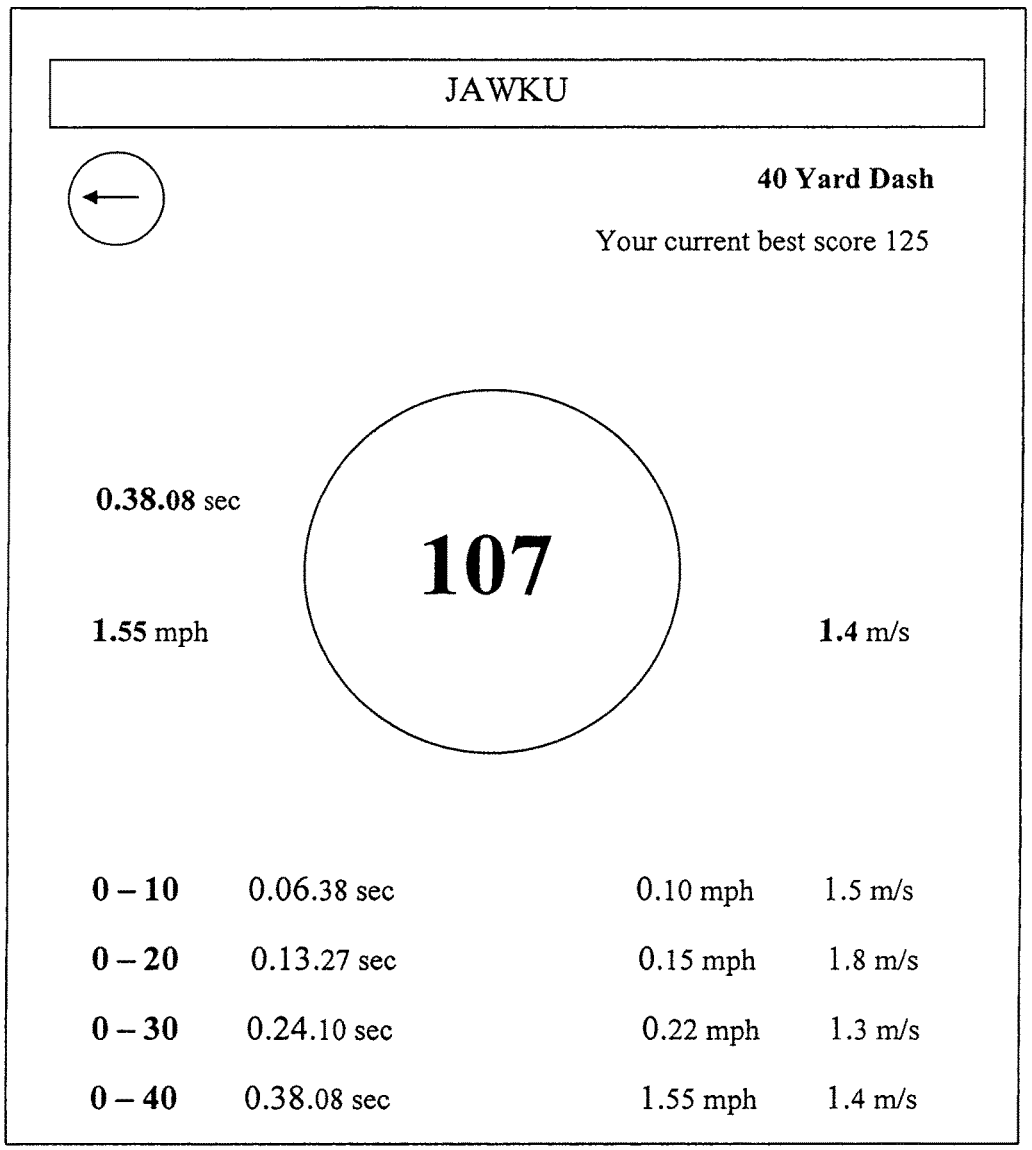
FIG. 27 is the FIG. 25 page showing the time and speeds achieved along with a JAWKU Score.

A specific current score known as the "Jawku Score" or "J Score™" is assigned for each test based on a number of predetermined psychological factors of each user. For example, FIG. 24 shows the participant has a current best score of 125 in the 40 yard dash. The participant by touching the running person symbol can pull up a display of three website pages for the 40 yard dash. The first page displayed is the start page depicted in FIG. 25. The next page shown in FIG. 26 is a progress page of time and speed achieved for the 10 yard and 20 yard distance covered. The third page viewed is that of FIG. 27 showing the complete record of speeds achieved over cumulative 10 yard intervals. In the example shown, the runner set a speed of 1.55 mph in 38.08 seconds for the 40 yard dash as determined by one of the Jawku motion sensor modules 3, 53 or 63: A Jawku Score of only 107 (considerably below his best of 125) was awarded, perhaps a reflection of a still healing knee injury.

The Jawku Score or "J-Score™" is based on a proprietary algorithm used as a ranking system and score generator. The "J-Score" has been calculated based on age and gender. As an example, the partial tables depicted in FIG. 32 and FIG. 33 show the results achieved for six different American/Canadian football exercises for males aged 12 and 16 with an overall percentile ranking achieved based on a proprietary "Jawku Score" algorithm for each exercise. Each test result is combined and weighted to produce the individual's percentile ranking. Similarly, Jawku Scores are generated for males ages 13, 14, 15, 17, 18 and 19. Older ages use the age 19 tables adjusted every 5-8 years to reflect older age groups. Similar tables are used for females.

An app is downloaded to the smartphone which shows after each test the percentile ranking and J-Score. The fitness website provides a data bank of all users who want to register their score to see where they rank amongst all Jawku users. The J-Score tables are imbedded in the apps logic. When a user completes a test a score can be generated based on the result. When a user completes two or more tests an average (mean) is taken from those tests to generate an overall score.

An example of an overall Jawku Score using the FIG. 33 table follows:
A 16 year old boy does the vertical jump and reaches 28 inches.
He is in the 70$^{th}$ percentile.
His J-Score is 8.
The same boy then does the 40-yard dash in 5.43 seconds.
He is in the 20$^{th}$ percentile.
His J-Score is 3.
His combined score is the average of 8 and 3.
His over-all J-Score is 5.5.
Then he Broad Jumps 8'2".
J-Score is 9.
His over-all J-Score is 6.75 (6.67 is rounded to the nearest 0.25 J-Score).

Interval Training

The Jawku™ website goal is to target the individual's needs and pair exercises and diet with the unique demands revealed by the provided user profile. Each exercise session is tailored to elicit a specific training response and develop each particular cardiovascular system required to achieve success. Jawku™ targets the user's cardio vascular system through conditioning exercises based on interval training. Interval training alternates between exercises requiring high intensity efforts with periods of "TRUE" recovery. This will take an individual from 65% of the max HR (heart rate) to 95% and then back to 65%.

Referring to FIG. 10, the STEP 4 assessment procedure calls for the user to conduct cardiovascular and weight strength exercises wherein the universal motion sensor modules are placed sequentially on the wrist, leg and chest. This assessment is based on "MET" or MET NUMBER which refers to the metabolic equivalent to exercise calories for each different type of activity.

The object is to obtain data representative of Heart Rate Numbers at VT(AT) and Peak VO2. The term "VT/AT)" refers to ventricle threshold/AT (anaerobic threshold) which is the maximum intensity level at which the body can supply adequate oxygen to the muscles. The term "Peak VO2" or "VO2 Max" refers to the maximum amount of oxygen consumed by the body during exercise. Jawku uses Peak VO2 testing to evaluate the cardiovascular fitness and aerobic endurance of those training like athletes. The three heart rate training zones (yellow, green and red) shown in FIG. 19 are dependent on these two critical heart rate numbers. The Yellow Zone representing a walking exercise is a low intensity heart rate zone used primarily for warm up, cool down, and recovery. The Green Zone representing a jogging exercise is a medium intensity heart zone used to train the exerciser in and around the exerciser's anaerobic threshold. The Red Zone representing a sprinting exercise is a high intensity heart rate zone. This zone pushes the user to train above the user's aerobic threshold just enough to elicit a positive training response. In order to truly see an increase in fitness the user must overload the body and this zone is designed to do just that. The above color zones are displayed on the smartphone of the exerciser in real time.

In doing the cardio assessment test of STEP 4, the user ideally can elect to use a home treadmill or a professional gym treadmill using the following treadmill instructions:
Treadmill assessment test instructions:
The user chooses the speed that can be held for 20 minutes (6-10 mph).
The heart rate sensor 64 is worn snugly on the core (chest) to track HR for a set time duration such as every 30 seconds.

Example: 7 mph

| Build speed (0-5 min) | Build Incline (5 min-END) |
|---|---|
| 0-1 min 3 mph | 5-5:30 min 1% incline stage 1 |
| 1-2 min 4 mph | 5:30-6 min 2% incline stage 2 |
| 2-3 min 5 mph | 6-6:30 min 3% incline stage 3 |
| 3-4 min 6 mph | 6:30-7 min 4% incline Stage 4 |
| 4-4:30 min 6.5 mph | 7-7:30 min 5% incline Stage 6-END |
| 4:30-5 min 7 mph | 2 min walking recovery at 3 mph |
| | Record: final HR. |

Alternatively, the user has the option of doing the cardio assessment without the treadmill by wearing the heart rate sensor in conjunction with an app on the smartphone that tells the user to slow down and speed up and to stay in the correct heart rate zone while doing the assessment.

At end of assessment a "2 Minute" HR recovery data is collected with treadmill set at 3 mph 0 degree incline.
Optimal recovery:
Persons HR falls 15% below AT.
If sub-optimal HR recovery is found this affects the user's individualized program design.
EXAMPLE of "TRUE" recovery period:
Starting HR 105:
(AT) HR 165
(PK) HR 195
220-age formula used.
A caveat is that if HR only drops 10% it is not a true recovery.

The cardio assessment uses the 220-Age calculation to provide the user's estimated HR. Several cardio template programs are used to create the app which modifies the max HR per individual while still carrying out the fitness goals. For example, if the individual's exercise program calls for:

5 min green zone
5 min yellow zone
3 min red zone
Repeat.

The app adjusts to the different percentages based on the age of the user.

It is important to note that a HR monitor is preferred to more accurately follow cardiovascular training zones.

As an alternative embodiment, the 6-DOF sensor module is designed to measure wattage. This data can be used for calculating and programming the app downloaded to the smartphone without use of a heart rate monitor.

As an alternative embodiment, the sensor module 3,53 need not be universal but separately provided for each wrist, ankle and body core (chest) to allow rapid shifting to save time and wear from for example, arm weight lifting to leg weight training.

Met and Calories Burned

The metabolic equivalent to exercise calories is MET for each different type of activity. MET is a relative measure of intensity. The formula for calories burned during exercise is as follows:

$$\text{Total Calories Burned} = \text{Duration (in minutes)} \times (\text{MET} \times 3.5 \times \text{weight in kg})/200$$

So, if a person weighing 68 kg did low impact aerobic exercises for 30 minutes, the calculation would be:

$$\text{Total Calories Burned} = 30 \text{ min} \times (\text{MET} \times 3.5 \times 68 \text{ kg})/200$$

To figure out the MET, C = calories burned, m=MET.

$$C = 30 \times (m \times 3.5 \times 68)/200$$

$$C = 30 \times (m \times 238)/200$$

$$C = 30 \times (m \times 1.19)$$

$$C = 35.7 \times m.$$

Using a built in calorie calculator as part of the app downloaded to the smartphone and selecting the correct information (68 kg for weight, aerobic, low impact and 30 minute duration) yields an answer of 180 calories.

$$180 = 35.7 \times m$$

Dividing each side by 35.7 yields the MET variable of 5.042017. As stated before, the MET is different for each different type of exercise and intensity level. This is why the value is an approximation and not exact. In FIG. 11 a running total of calories burned during a day's exercise program may be viewed. Similarly, a cumulative total of calories burned for a completed workout set may be viewed on the smartphone.

According to the Compendium of Physical Activities (online website Https://sites.google.com/site/compendiumof physical activities/) the MET NUMBER for basic easy running is 4.97±1.23 and changes to 5.69±1.34 for basic medium running. By determining the person's VO2 Max, Jawku's proprietary algorithms are able to determine a wide range of values such as how many calories a person burns, their fitness level, speed and distance ability and MET capabilities.

Peak Power

The second assessment called for in STEP 4 is a weight strength exercise used to measure peak power. Power is an output of how much force a person can generate in a brief amount of time. Strength times speed equals power or mass times velocity equals power. This is peak power.

Peak power in this case can be looked at as a 1RM (I Rep Maximum). Anything less than peak power or 1RM can be related to a percentage of the 1RM (100%). A table shown in FIG. 28 accessed by the user's smartphone acts as the preliminary assessment tool for the user to establish a 1RM, and then the weights to be lifted can automatically be calculated or suggested on the viewing screen of the smartphone.

The viewer uses the FIG. 28 table as follows. User will find the number of reps to concentric failure that can be performed with a certain weight. This table can be used as an assessment tool by the user for the NFL Scouting Combine test for repetitions to failure for a 225 lbs. bench press. For example, if the user can only do eight reps lifting a weight and could not possibly do another full rep, that is the user's point of failure. The user then clicks on the percentage associated with that number of repetitions from the table. The user is also instructed to enter the assessment weight.

Once the user clicks on their reps achieved, the app in the smartphone automatically divides the weight the user lifted by that percentage using decimals (for example, 83% equals 0.83) and that provides an approximation of the user's one repetition maximum. For example, if the individual can perform 10 reps with 175 lbs. in the bench press, that means that 175 lbs. is 75% (0.75) of their one repetition maximum. So the app using the above table divides 175 lbs by 0.75 which yields 233 lbs. as the one rep maximum.

The subsequent program that follows then give the user the suggested weight based on percentages. For example, if the user's 1RM for a Lat pull down is 155, and "Body Builder" was selected from the six profile alternatives chosen, the template for body builder would look as shown in FIG. 29, wherein set 1 is 60% for 15 reps, set 2 is 70% for 12 reps, set 3 is 80% for 10 reps and set 4 is 85% for 8 repetitions.

Unload Equations

Often a tapering of an athlete's training sessions is scheduled for several days prior to an in-season or opening game day to avoid overtraining. An "unload equation" is used to calculate a new lower 1RM. These equations are different for 4 commonly used different Bench Press exercises.

As an example, for a 1 Rep Max for a Flat Barbell Bench Press the formula used is:

$$(\text{Weight} \times \text{Reps} \times [0.0333]) + \text{Weight}$$

wherein Weight=the Heaviest weight the individual can safely lift, Reps=the amount of full reps completed and 0.0333=Constant. If 315 lbs. is the individual's weight lifted and 5 reps are completed, the above formula yields 367.4 lbs as the 1Rep max.

The unload equation used is:

[(Weight×Reps×[0.0333])+Weight]×0.64.

Note that the unload equation above uses an additional constant of 0.64 which yields 367.4 lbs. X 0.64=235 lbs. as the unload weight to be lifted.

As an example, for a 1 Rep Max Inclined Barbell Bench Press the formula used is:

[(Weight×Reps×[0.0333])+Weight]×0.8.

Assuming weight lifted is 315 lbs and 5 reps are completed, the formula yields 294 lbs. weight to be lifted. The unload equation uses the additional multiplying constant of 0.64 to yield 188 lbs. as the 1 Rep Max Unload weight to be lifted. The unload equation is:

[[(Weight×Reps×0.0333)+Weight]×0.8]×0.64.

In another example, for a 1 Rep Max Dumbbell Flat Bench Press, the formula is:

$$\frac{(\text{Flat BB Bench Press 1 } RM)}{2} \times 0.9$$

Example (367 lbs/2)×0.9=165 lbs 1 Rep Max

Multiplying 165 lbs×0.64 yields 105.6 lbs. as the unload weight each hand lifts.

In another example for a 1 Rep Max Dumbbell Incline exercise, the unload equation is:

$$\frac{(\text{Incline BB Bench Press 1 } RM)}{2} \times 0.9$$

Example (294 lbs/2)×0.9=132 lbs 1 Rep Max

Multiplying 132 lbs×0.64 yields 84.5 lbs as the unload weight each hand lifts.

The weight lifter used in the Unload Equations examples, first places the magnetic motion sensor module 3 or 53 held in the FIG. 3 cradle 10 on the 315 lbs. barbell weight. The weight lifter next activates the sensor module and performs the 5 reps of the flat barbell bench press exercise and the incline barbell bench press exercise. The weight lifter then pulls up on the screen of the user's smartphone the template page shown in FIG. 30. The user enters the weight lifted for the flat and incline barbell bench press exercises. The smartphone has an app using the above equations which calculates the 1 Rep Max weight and the 1 Rep Max unload weight to be lifted for each type bench press exercise and displays the filled template as shown in FIG. 31. The sensor module automatically enters the reps completed. The above is repeated for the dumbbell weights being lifted.

Pushups

Pushups are another exercise generating biometric data sensed by the 6-DOF sensor module. Primarily, pushups in their various forms are calisthenics exercises used to build strength and endurance. Pushups are sometimes measured by various forms of Sport Combines aside from American/Canadian Football. The user is instructed to perform a series of pushups. The first pushup measured will be a maximal effort to retrieve Peak Power. The sensor module is best worn about the sternum using the chest mounted sensor module. A range of movement is measured from 0-18.0 inches. The pushup velocity is measured in units of mph or kph. A range of velocity is set at 0-250mph or 0-500 kph.

Push up Power can be represented by the formula:

$$\frac{\text{Work}(N)}{\text{time}(t)} = \text{Power}$$

where Work(n) is Pushup Repetitions and time(t) is minutes. The maximum number of pushups achieved in a unit of time, such as one minute represents Pushup Peak Power expressed as Maximal Pushups per Minute. A chart (not shown) is viewable on the smartphone showing the repetition number of pushups suggested to be attempted over 5-10 minute intervals as a percentage of the Maximal Pushups per Minute rate of repetition.

Olympic Power Clean

An example of an Olympic exercise by which the user generates 6-DOF biometric motion data is the Olympic Power Clean. The user places the 6-DOF sensor module in the magnetic cradle 10 of FIG. 3 and mounts the same on the barbell to be lifted. The user pulls up a website page (not shown) using the user's smartphone and enters the weight of the barbell.

The user engages in a power clean using correct technique to perform one hang clean. The user begins when the sensor module signal alerts the user. The sensor module tracks peak power as a percentage of power based on each repetition. The app in the smartphone sets a range of 0-100.0 inches and a velocity range in units of mph of 0-50 mph or a range in kph of 0-100 kph.

Power can be represented by the formula:

$$\frac{\text{Work }(N)}{\text{time }(t)} = \text{Power.}$$

An alert can be set by the app when the repetition is less than 85% of peak power.

NFL Scouting Combine Tests

Examples that follow of the biometric motion data gathered by the 6-DOF sensor module and sent to the smartphone are for exercises modeled after the NFL Scout Combine tests. The data are interpreted by an app using mathematical equations and formulas for calculations by the Jawku proprietary 6-DOF algorithms. The exercises monitored include the vertical jump, horizontal/broad jump, 40 yard dash (timed at 10, 20 30 and 40 yd intervals), 20 yard shuttle (also called the 5-10-5), 60 yard shuttle (also called the 15-30-15), and the three cone drill (also called the L-Drill). The 225 lbs. bench press counts repetitions to failure with reps counted using the Jawku 6-DOF sensor module. The 20 yard shuttle, 60 yard shuttle and three cone drill tests are monitored using the Jawku 6-DOF sensor with results calculated using algorithms similar to the 40 yard dash and as such are not discussed further.

1. Vertical Jump

The athlete while wearing the 6-DOF sensor module establishes a standing position. Upon the sensor module signaling the system is ready, the athlete performs a full countermovement vertical jump. The athlete will attempt to jump as high as possible. The sensor module measures flite time and jump height. The flite time is measured in units of seconds and the flite time range is set at 0.00-5.00 seconds. The jump height is measured in either inches or centimeters. Using a toggle, the jump range is set at 1.00-60.00 inches and at 3.00-152.40 centimeters.

The data collected is recorded to the fitness website and displayed to the athlete's smartphone. These are the vital measurements output from the exercise as well as the formulas used during coding the app:

Flight time $$\text{Time}_{landing} - \text{Time}_{takeoff} = X.XX \text{ sec}$$

Jump Height $$\text{Height}_{Peak} - \text{Height}_{reach} = X.XX \text{ inches}$$

$$\left(\frac{g * (\text{Time}_{flight})^2}{8}\right) = X.XX \text{ inches (Flite time calculation)}.$$

2. Horizontal (Broad) Jump

The athlete while wearing the 6-DOF sensor module establishes a standing position behind the start line. Upon the sensor module signaling the system is ready, the athlete performs a full countermovement horizontal jump. The athlete jumps to the right, resets and jumps again to the left. The athlete attempts to jump as far as possible. The jump range is measured in feet and inches and using a toggle is also measured in meters. The jump range is set at 0-20 feet and 0-11.9 inches with a meters range set at 0-12.2 meters.

The data collected is recorded to the fitness website and displayed to the athlete's smartphone. The vital measurement output from the exercise is the jump distance traveled in the air as measured in feet and inches or meters. This exercise is sometimes called the standing long jump. Two jumps are attempted.

3. 40 Yard Dash

The athlete while wearing the 6-DOF sensor module establishes a start position and sprints 40 yards as fast as possible. The sensor module signals the athlete alerting the athlete when to go. The sensor module tracks times at 10 yards, 20 yards, 30 yards and 40 yards. Time starts to record once the sensor module is ready.

The 40 yard dash time is measured in units of seconds. The seconds range is set at 0-9.99 seconds. A peak velocity is measured in units of mph, kph, or m/s. The velocity range is set at 1-29.99 mph, 1-48.28 kph and 1-13.4 m/s using a toggle.

A peak acceleration is measured in units of m/s^2 or G's using a toggle. The acceleration range is set at m/s^2: 0-30.0 m/s^2 or 0-4.10 G's, The same settings of seconds range, velocity range and acceleration range are used to measure the start-10 yard split, the start 10-yard average velocity and the start-10 yards average acceleration. This also applies to the measurements of the 10-20 yard split, the 20-30 yard split and the 30-40 yard split.

The data collected for the 40 yard dash is recorded to the fitness website and displayed to the athlete's smartphone.

These are the vital measurements output from the exercise as well as the formulas used during coding the app:

40 yd Time (All Collection Systems)

Start-10yd split (Timing system)

Average Velocity $$\frac{10 \text{ yds}}{10 \text{ yd gate time}} * (2.04545455) = X.XX \text{ mph}$$

Average Velocity $$\frac{10 \text{ yds}}{10 \text{ yd gate time}} * (2.04545455) = X.XX \text{ mph}$$

$$\frac{10 \text{ yds}}{10 \text{ yd gate time}} * (3.29184) = X.XX \text{ kph}$$

$$\frac{10 \text{ yds}}{10 \text{ yd gate time}} * (.9144) = X.XX \frac{m}{s}$$

Average Acceleration $$\frac{\left(\frac{10 \text{ yds}}{10 \text{ yd gate time}}\right) * 0.9144}{10 \text{ yd gate time}} = X.XX \frac{m}{s^2}$$

$$\frac{\left(\frac{10 \text{ yds}}{10 \text{ yd gate time}}\right) * 0.9144}{10 \text{ yd gate time}} = X.XX \frac{m}{s^2}$$

$$\left(\frac{\left(\frac{10 \text{ yds}}{10 \text{ yd gate time}}\right) * 0.9144}{10 \text{ yd gate time}}\right) * 0.101971621 = X.XX \text{ g}$$

20-30 yd Split (Timing System)

Average Velocity $$\frac{10 \text{ yds}}{30 \text{ yd gate time} - 20 \text{ yd gate time}} * (2.04545455) = X.XX \text{ mph}$$

$$\frac{10 \text{ yds}}{30 \text{ yd gate time} - 20 \text{ yd gate time}} * (3.29184) = X.XX \text{ kph}$$

$$\frac{10 \text{ yds}}{30 \text{ yd gate time} - 20 \text{ yd gate time}} * (.9144) = X.XX \frac{m}{s}$$

Average Acceleration $$\frac{\left(\frac{10 \text{ yds}}{30 \text{ yd gate time} - 20 \text{ yd gate time}}\right) * 0.9144}{30 \text{ yd gate time} - 20 \text{ yd gate time}} = X.XX \frac{m}{s^2}$$

$$\frac{\left(\frac{10 \text{ yds}}{30 \text{ yd gate time} - 20 \text{ yd gate time}}\right) * 0.9144}{30 \text{ yd gate time} - 20 \text{ yd gate time}} = X.XX \frac{m}{s^2}$$

$$\left(\frac{\left(\frac{10 \text{ yds}}{30 \text{ yd gate time} - 20 \text{ yd gate time}}\right) * 0.9144}{30 \text{ yd gate time} - 20 \text{ yd gate time}}\right) * 0.101971621 = X.XX \text{ g}$$

30-40 yd Split (Timing System)
  Average Velocity $$\frac{10 \text{ yds}}{40 \text{ yd gate time} - 30 \text{ yd gate time}} * (2.04545455) = X.XX \text{ mph}$$

$$\frac{10 \text{ yds}}{40 \text{ yd gate time} - 30 \text{ yd gate time}} * (3.29184) = X.XX \text{ kph}$$

$$\frac{10 \text{ yds}}{40 \text{ yd gate time} - 30 \text{ yd gate time}} * (.9144) = X.XX \frac{\text{m}}{\text{s}}$$

Average Acceleration $$\frac{\left(\frac{10 \text{ yds}}{40 \text{ yd gate time} - 30 \text{ yd gate time}}\right) * 0.9144}{40 \text{ yd gate time} - 30 \text{ yd gate time}} = X.XX \frac{\text{m}}{\text{s}^2}$$

$$\frac{\left(\frac{10 \text{ yds}}{40 \text{ yd gate time} - 30 \text{ yd gate time}}\right) * 0.9144}{40 \text{ yd gate time} - 30 \text{ yd gate time}} = X.XX \frac{\text{m}}{\text{s}^2}$$

$$\left(\frac{\left(\frac{10 \text{ yds}}{40 \text{ yd gate time} - 30 \text{ yd gate time}}\right) * 0.9144}{40 \text{ yd gate time} - 30 \text{ yd gate time}}\right) * 0.101971621 = X.XX \text{ g}$$

The above 40 yard dash results are broken up, recorded to the fitness website and displayed to the athlete's smartphone as follows:
  Trial Type (All Collection Systems)
  40 yd (All Collection Systems)
    Split time (sec)
    Peak (Timing System)
      Velocity (mph -OR- kph -OR- m/s)
      Acceleration (m/s^2 -OR- g's)
    Start-10 yd (Timing System)
      Split time (sec)
      Average split Velocity (mph -OR- kph -OR- m/s)
      Average split Acceleration (m/s^2 -OR- g's)
    10-20 yd (Timing System)
      Split time(sec)
      Average split Velocity (mph -OR- kph -OR- m/s)
      Average split Acceleration (m/s^2 -OR- g's)
    20-30 yd (Timing System)
      Split time(sec)
      Average split Velocity (mph -OR- kph -OR- m/s)
        Average split Acceleration (m/s^2 -OR- g's)
    30-40 yd (Timing System)
      Split time (sec)
        Average split Velocity (mph -OR- kph -OR- m/s)
        Average split Acceleration (m/s^2 -OR- g's).

Data Conversion and Dynamic Drift Correction

The biometric data generated by the JAWKU 6-DOF sensor is processed by the application running on either a smartphone or the JAWKU website. The raw accelerometer and gyroscope data is referenced to the coordinate system associated with the moving sensor frame, and not the required earth reference frame. Once the sensor data file is fully uploaded to the smartphone via Low Energy Bluetooth (LEB), the raw accel/gyro data is transformed to the earth frame via a 3×3 coordinate matrix transform. Once transformed to the earth frame, the gravity component of the accelerometer data is removed, leaving only the actual acceleration associated with the sensor/body movement. With the gravity component removed, the accelerometer data is reduced to a single vertical and horizontal component from the initial X, Y, Z accelerometer components. The vertical and horizontal components of the acceleration are used to calculate the various biomechanical elements for the movement under study.

The data format for sensor to smartphone is described as follows. There are only two types of packets from the sensor. The header packet contains the scaling and filtering information for the remainder of the packets to be uploaded. The format of the header packet is shown below:
|Arange(byte0)|Grange(byte1)|sample period(byte2)|temperature(byte3)|# of sample frames(bytes4-5)|.

The packet bytes are described as follows:
Byte 0—Arange—this is the range of the accelerometer, 2/4/6/8/16 g
Byte 1—Grange—Gyroscope range, 250/500/2000 degrees/sec
Byte 2—sample rate, 10/20/50 samples/sec or 100/50/20 msec/sample
Byte 3—temperature
Byte 4-5—# of sample packets following the $0^{th}$ packet.

The format of the $0^{th}$ thru $N^{th}$ data sample packet is shown below:
|frame #(bytes0-1)|Ax L (byte2)|Ax H(byte3)|Ay L(byte4)|Ay H(byte5)|Az L(byte6)|Az H(byte7)|
|ωx L(byte8)|ωx H(byte9)|ωy L(byte10)|ωy H(byte11)|ωz L(byte12)|ωz H(byte13)|.

The sample packet bytes are described as follows:
Bytes 0-1—frame # of current frame, starts at 0, ends at N−1, where N is given in bytes 4-5 of the header packet
Byte 2—Accel x low byte
Byte 3—Accel x high byte
Byte 4—Accel y low byte
Byte 5—Accel y high byte
Byte 6—Accel z low byte
Byte 7—Accel z high byte
Byte 8—Gyro x low byte
Byte 9—Gyro x high byte
Byte 10—Gyro y low byte
Byte 11—Gyro y high byte
Byte 12—Gyro z low byte
Byte 13—Gyro z high byte.

The $0^{th}$ sample packet gyro values, bytes 8-13, are set to zero. This is due to the $0^{th}$ packet representing the static orientation of the sensor at the beginning of the sample period. The initial static orientation of the sensor is derived from this sample as the accelerometer data only includes gravity vector data. The rotation is represented by the three Euler angles, which are defined as CCW rotations about the X', Y', and Z' axes of the coordinate system associated with the sensor. Once the initial orientation is known, pitch and roll angles, the orientation of subsequent packets is determined by adding the detected gyro rotation associated with each sample packet to this initial value. The continuous calculation of the current sensor orientation is required to allow the gravity component to be continuously removed from the accelerometer data once the vector components are transformed to the earth reference system X, Y, and Z.

An example of a technique to identify conditions to reestablish the orientation of the sensor independent of the gyro data is next described. This orientation reset will minimize the effect of gyro drift over the course of the sample period, albeit small given the short duration of the sampled event. First, a determination of the initial orientation of the sensor relative to earth coordinates is made.

In order to determine the vertical and horizontal components of the measured acceleration in the earth frame coordinates X, Y, and Z axes, the real-time component of the gravity vector must be subtracted from the raw acceleration data. To facilitate this, the sensor begins to sample and store the 6-DOF sensor accelerometer and gyro data once the start button on the sensor is pushed. Once pushed, the sensor data is continuously sampled and stored to the sensor FIFO buffer (chip 25) with the FIFO buffer being capable of storing several minutes of the 6-DOF data. As each sample is stored to the FIFO, the scalar values of the 3 gyro vectors are continuously monitored. If it is found that all three gyro vector magnitudes are below or equal to a predetermined noise floor of the sensor, it can be assumed that the sensor, and associated body segment, is static or not moving.

The logic used here is based on the fact that all human motion is derived from joint rotation and not linear motion. It is very difficult, if not impossible, for a body part to be moving without a rotational component. If the sensor is static, there is no rotation about any of the sensor axes resulting in no acceleration component associated with the sensor axis. This condition results in the sample containing ONLY the contribution from the gravity vector. If this condition is detected, the current sample becomes the $0^{th}$ sample packet in the current motion capture sequence and will be used to calculate the initial roll angle $\varphi$, rotation about the sensor X' axis and the pitch angle $\theta$, rotation about the Y' axis. It must be noted that the Yaw angle $\psi$, rotation about the Z' axis cannot be determined by a 6 DOF sensor but requires an additional 3 axis magnetometer to create a 9-DOF sensor. Fortunately, this is not a problem for this application as only the vertical component, Z axis, and the horizontal component, combination of the X and Y axes, are required.

Due to only the roll and pitch angles being required, the 3D matrix transform can be represented by a simple 3×3 rotation matrix shown as $$\begin{bmatrix} V_X \\ V_Y \\ V_Z \end{bmatrix} = \begin{bmatrix} \cos\theta & \sin\varphi\sin\theta & \cos\varphi\sin\theta \\ 0 & \cos\varphi & -\sin\varphi \\ -\sin\theta & \sin\varphi\cos\theta & \cos\varphi\cos\theta \end{bmatrix} \begin{bmatrix} V_X' \\ V_Y' \\ V_Z' \end{bmatrix} \quad \text{eqn. 1}$$

where $V_X$, $V_Y$, and $V_Z$ are the vector components in earth referenced coordinates (X,Y,Z), $V_X'$, $V_Y'$, and $V_Z'$ are the measured vector components in the sensor frame (X',Y',Z'), roll angle $\varphi$, and pitch angle $\theta$.

Normally the $V_X'$, $V_Y'$, $V_Z'$ values measured by the sensor accelerometer components are given as $$V_X' = G'(x) + A'(x) + N'(x)$$

$$V_Y' = G'(y) + A'(y) + N'(y)$$

$$V_Z' = G'(z) + A'(z) + N'(z) \quad \text{eqn. 2}$$

where G'(x,y,z) are the gravity vector components tangent to X', Y', and Z' sensor axes, respectively. A'(x,y,z) are the desired motion induced acceleration vector components again tangent to the sensor axes, respectively. The random noise components N'(x,y,z) of the measurements can be neglected at this time.

If it is assumed that the acceleration components, A'(x,y,z) are zero, and the noise is neglected in eqn. 2, the sensor measurements represent only the gravity vector components in the X', Y', Z' sensor frame represented as $$\begin{bmatrix} V_X' \\ V_Y' \\ V_Z' \end{bmatrix} = \begin{bmatrix} G'(x) \\ G'(y) \\ G'(z) \end{bmatrix} \quad \text{eqn. 3}$$

By definition, the gravity vector in the earth referenced frame is given as $$\begin{bmatrix} V_X \\ V_Y \\ V_Z \end{bmatrix} = \begin{bmatrix} G_X \\ G_Y \\ G_Z \end{bmatrix} = \begin{bmatrix} 0 \\ 0 \\ 1 \end{bmatrix} \quad \text{eqn. 4}$$

Where the full gravity vector G is tangent to the earth reference Z axis with the X and Y components zero resulting in $G_Z = G$. Inserting eqns. 3 and 4 into eqn. 1 and solving for $\varphi$ and $\theta$ results in $$\varphi_0 = \tan^{-1}\frac{G'(y)}{G'(z)} \quad \text{eqn. 5}$$

$$\theta_0 = \tan^{-1}\frac{-G'(x)}{(G'(y)\sin\varphi + G'(z)\cos\varphi)} \quad \text{eqn. 6}$$

where $\varphi_o$ and $\theta_o$ are the initial roll and pitch angles associated with the $0^{th}$ sample packet.

Recall that the $0^{th}$ sample packet has the three gyro rotations values set to zero as they are ignored for the $0^{th}$ sample packet only. As the arctangent is being used, the sign of both arguments must be used to determine which quadrant the actual angle resides.

With the initial angle calculated from the $0^{th}$ sample packet, the gyro data is used in the subsequent sample packets to calculate the current sensor orientation. For each sample packet, the current roll and pitch angles are calculated by adding the incremental changes in the two Euler angles associated with the X' and Y' axes of the sensor gyro as $$\varphi_N = \varphi_{N-1} + (\omega_{NX} * t_{sample}) \quad \text{eqn. 7}$$

$$\theta_N = \theta_{N-1} + (\omega_{NY} * t_{sample}) \quad \text{eqn. 8}$$

where $\omega_{NX}$ and $\omega_{NY}$ are the rotation rates in degrees/sec of the $N^{th}$ sample, as measured by the sensor gyro, around the X' and Y' sensor axes, respectively, $t_{sample}$ is the sensor sample rate as given in the header packet With $\varphi_N$ and $\theta_N$ calculated, the current Nth sample can be transformed from the sensor frame back to the earth frame with eqn. 1 as $$V_{NX} = A_{NX} = V_{NX}'(\cos\theta_N) + V_{NY}'(\sin\varphi_N \sin\theta_N) + V_{NZ}'(\cos\varphi_N \sin\theta_N) \quad \text{eqn. 9}$$

$$V_{NY} = A_{NY} = V_{NY}'(\cos\varphi_N) - V_{NZ}'(\sin\varphi_N) \quad \text{eqn. 10}$$

$$V_{NZ} = (A_{NZ} + G) = -V_{NX}'(\sin\theta_N) + V_{NY}'(\sin\varphi_N \cos\theta_N) + V_{NZ}'(\cos\varphi_N \cos\theta_N) \quad \text{eqn. 11}$$

where $A_{NX}$, $A_{NY}$, and $A_{NZ}$ are the desired motion induced accelerations represented in the earth reference frame via the calculated $\varphi_N$ and $\theta_N$ roll and pitch angles for the $N^{th}$ sample. Note that the full gravity vector G must be subtracted from the $V_{NZ}$ component to extract the Z acceleration component, $A_{NZ}$.

Finally, the vertical and horizontal acceleration components in the earth reference frame can be expressed as $$A_{Nvertical} = A_{NZ} \qquad \text{eqn. 12}$$

$$A_{Nhorizontal} = (A_{NX}^2 + A_{NY}^2)^{1/2} \qquad \text{eqn. 13.}$$

From this now acceleration data presented in the earth frame coordinates the vertical and horizontal velocities can be determined via $$U_N = U_{N-1} + (A_N * t_{sample}) \qquad \text{eqn. 14}$$

where $U_N$ is the velocity magnitude for the $N^{th}$ sample. p In a similar fashion, the vertical and horizontal displacements can be determined via $$D_N = D_{N+1} + \left(\frac{1}{2} A_N * t_{sample}^2\right) \qquad \text{eqn. 15}$$

where $D_N$ is the linear displacement for the $N^{th}$ sample. It must be noted that the constants of integration have been set to zero, initial velocity and displacement are assumed to be zero at t=0.

What follows in an example of the data transferred from the sensor to the smartphone application. The first packet from the sensor is the header packet with the format shown as:

|Arange(byte0)|Grange(byte1)|sample period(byte2)|temperature(byte3)|# of sample frames(bytes4-5)|.

The packet bytes are described as follows:

Byte 0—Arange—this is the FS range of the accelerometer, 0=2 g, 1=4 g, 3=6 g, 4=8 g, 5=16 g Byte 1—Grange—Gyroscope FS range, 0=250 dps, 1=500 dps, 2=2000 dps, (dps=degrees/sec)

Byte 2—sample rate, 0=10 s/sec, 1=20 s/sec, 3=50 s/sec (s/sec=samples/sec) or 100/50/20 msec/sample Byte 3—temperature is given in 8 bit 2's compliment, +/−127°

Byte 4-5—# of sample packets following the header packet.

The format of the $0^{th}$ thru $N^{th}$ data sample packet is shown below:

|frame #(bytes0-1)|Ax L (byte2)|Ax H(byte3)|Ay L(byte4)|Ay H(byte5)|Az L(byte6)|Az H(byte7)|Gx L(byte8)|Gx H(byte9)|Gy L(byte10)|Gy H(byte11)|Gz L(byte12)|Gz H(byte13)| sample data:
|0|0|-|5E|71|-|22|49|-|2B|0A|-|00|00|-|00|00|-|00|00|
|1|0|-|52|71|-|2A|49|-|29|0C|-|55|22|-|82|DF|-|77|81|
|2|0|-|50|70|-|20|49|-|19|0C|-|60|22|-|74|DF|-|75|81|
|3|0|-|53|70|-|20|49|-|18|0C|-|61|22|-|76|DF|-|00|80|
|4|0|-|52|70|-|19|49|-|18|0C|-|62|22|-|77|DF|-|02|80|

The frame #, bytes 0-1 is given in unsigned 16 bit, the accelerometer and gyro data, bytes 2-13, are given in 16 bit, 2's compliment. Extracting the values from sample 0 yields:

Sample 0

|0|0|-|5E|71|-|22|49|-|2B|0A|-|00|00|-|00|00|-|00|00|
sample #=00=$0^{th}$ sample
Ax=715Eh=29022
Ay=4922h=18722
Az=0A2Bh=2603
Gx=00=n/a
Gy=00=n/a
Gz=00=n/a Note that sample 0 has the gyro data set to zero as the accelerometer data represents only the gravity vector. The initial $\varphi_0$ and $f_0$ via eqns. 5 and 6 are respectively:

$$\varphi_0 = \tan^{-1} \frac{G'(y)}{G'(z)}$$

$$\varphi_0 = \tan^{-1}(18722/2603) = 82.1°$$

$$\theta_0 = \tan^{-1} \frac{-G'(x)}{(G'(y)\sin\varphi + G'(z)\cos\varphi)}$$

$$\theta_0 = \tan^{-1}[-29022/\{(18722 \sin 82.1) + (2603 \cos 82.1)\}] = -56.9°.$$

Due to no acceleration component in the $0^{th}$ sample, the magnitude of the G vector in terms of the sensor LSB's is determined by:

$$G = G_z = [(29022)^2 + (18722)^2 + (2603)^2]^{1/2} = 34635 \text{ LSBs.}$$

G must be subtracted from $V_{NZ}$ once the V' is transformed to V via eqn. 11 for all subsequent samples 1 thru N.

Sample 1

|1|0|-|52|71|-|2A|49|-|29|0C|-|55|22|-|82|DF|-|77|81|
sample #=01=$1^{st}$ sample (note: all values are in LSBs)
Ax=7152h=29010
Ay=492Ah=18730
Az=0C29h=3113
Gx=2255h=8789
Gy=DF82h=−8318
Gz=8177h=−32393.

Via the header packet, assume the gyro FS sensitivity co is given as 500 dps or $17.50 \times 10^{-3}$ dps/LSB and $t_{sample}$=50 msec/sample. The new orientation angles $\varphi_1$ and $\theta_1$ via eqns. 7 and 8 are calculated, respectively:

$$\varphi_1 = \varphi_0 + \omega_{x1} * t_{sample} = 82.1° + (8789 * 17.5 \times 10^{-3} * 50 \times 10^{-3}) = 82.1 + 7.69 = 89.79° \text{ and}$$

$$\theta_1 = \theta_o + \omega_{y1} * t_{sample} = -56.9° + (-8318 * 17.5 \times 10^{-3} * 50 \times 10^{-3}) = -56.9 - 7.28 = -64.18°.$$

Using the calculated angles, the V' vector components can be transformed to the earth frame V vector components via eqns. 9, 10, 11 as shown below:

$$V_{NX} = A_{NX} = V_{NX}'(\cos \theta_N) + V_{NY}'(\sin \varphi_N \sin \theta_N) + V_{NZ}'(\cos \varphi_N \sin \theta_N)$$

$$V_{1X} = 29010 \cos(-64.18) + 18730 \sin(89.79)\sin(-64.18) + 3113 \cos(89.79)\sin(-64.18) = -42146 \text{ LSBs}$$

$$V_{NY} = A_{NY} = V_{NY}'(\cos \varphi_N) - V_{NZ}'(\sin \varphi_N)$$

$$V_{1Y} = 18730 \cos(89.79) - 3113 \sin(-64.18) = 28709 \text{ LSBs}$$

$$V_{NZ} = -V_{NX}'(\sin \theta_N) + V_{NY}'(\sin \varphi_N \cos \theta_N) + V_{NZ}'(\cos \varphi_N \cos \theta_N) - G$$

$$V_{1Z} = -29010 \sin(-64.18) + 18730 \sin(89.79)\cos(-64.18) + 3113 \cos(89.79)\cos(-64.18) - 34635 = -358 \text{ LSBs.}$$

From these earth frame components, the vertical and horizontal components of the acceleration are calculated via eqns. 12 and 13, respectively. Letting G=9.8 m/sec² :

$$A_{1V} = A_{1Z} = -358 * 0.122 \times 10^{-3} G/\text{LSB} = -43.735 \times 10^{-3} G = -0.4286 \text{ m/sec}^2$$

$$A_{1H} = (A_{1X}^2 + A_{1Y}^2)^{1/2} = [(28709)^2 + (-358)^2]^{1/2} * 0.122 \times 10^{-3} G/\text{LSB} = 3.50 G = 34.4 \text{ m/sec}^2.$$

As can be seen in this example, the acceleration is primarily in the horizontal plane with a very small downward component via the Z component.

Finally, the vertical and horizontal speed and displacement is calculated via eqns. 14 and 15, respectively.

$$U_{1V} = A_{1V} * t_{sample} = -0.4286 \times 10^{-3} * 50 \times 10^{-3} = -0.0214 \text{ m/sec}$$

$$D_{1V} = 1/2 A_{1V} t^2_{sample} = 1/2 * 0.4286 \times 10^{-3} * (50 \times 10^{-3})^2 = -536 \times 10^{-6} \text{ m} = -536 \text{ μm (microns)}$$

$$U_{1H} = A_{1H} * t_{sample} = 34.3 * 50 \times 10^{-3} = 1.715 \text{ m/sec}$$

$$D_{1H} = 1/2 A_{1H} t^2_{sample} = 1/2 * 34.3 * (50 \times 10^{-3})^2 = 42.88 \times 10^{-3} \text{ m} = 42.88 \text{ mm (millimeters)}.$$

This process is repeated for each Nth sample.

Sample 2

|2|0|-|50|70|-|20|49|-|19|0C|-|60|22|-|74|DF|-|75|81|
sample #=02=$2^{nd}$ sample
Ax=7050h=28752
Ay=4920h=18720
Az=0C19h=3097
Gx=2260h=8800
Gy=DF74h=-8332
Gz=8175h=-32395
determine $\varphi_2$ and $\theta_2$:

$$\varphi_2 = \varphi_1 + \omega_{x2} * t_{sample} = 89.79° + (8800 * 17.5 \times 10^{-3} * 50 \times 10^{-3}) = 97.49°$$

$$\theta_2 = \theta_1 + \omega_{y2} * t_{sample} = -64.18° + (-8332 * 17.5 \times 10^{-3} * 50 \times 10^{-3}) = -71.47°.$$

Sample 3

|3|0|-|53|70|-|20|49|-|18|0C|-|61|22|x|76|DF|-|00|80|
sample #=03=$3^{rd}$ sample
Ax=7053h=28755
Ay=4920h=18720
Az=0C18h=3096
Gx=2261h=8801
Gy=DF76h=-8330
Gz=8000h=-32768
determine $\varphi_3$ and $\theta_3$:

$$\varphi_3 = \varphi_2 + \omega_{x3} * t_{sample} = 97.49° + (8801 * 17.5 \times 10^{-3} * 50 \times 10^{-3}) = 105.19°$$

$$\theta_3 = \theta_2 + \omega_{y3} * t_{sample} = -71.47° + (-8330 * 17.5 \times 10^{31\ 3} * 50 \times 10^{-3}) = -78.76°.$$

Sample 3

|4|0|-|52|70|-|19|49|-|18|0C|-|62|22|-|77|DF|-|02|80|
sample #=04=$4^{th}$ sample
Ax=7052h=28754
Ay=4919h=18713
Az=0C18h=3096
Gx=2262h=8802
Gy=DF77h=-8329
Gz=8002h=-32766
determine $\varphi_4$ and $\theta_4$:

$$\varphi_4 = \varphi_3 + \omega_{x4} * t_{sample} = 105.19° + *8802 * 17.5 \times 10^{-3} * 50 \times 10^{-3} = 112.89°$$

$$\theta_4 = \theta_3 + \omega_{y4} * t_{sample} = -78.76° + (-8329 * 17.5 \times 10^{-3} * 50 \times 10^{-3}) = -86.05°.$$

During the motion period under study, occasionally the user's body segment will randomly be static for one or more sample periods, i.e. change in direction requires the motion to be zero at the inflection point. This condition is easily detected in that all three gyro axes will record no rotation with the individual gyro axes values being zero, or below the predetermined noise floor. When these samples are seen during the data reduction process, the current orientation of the sensor can be calculated via the same process as described for the $0^{th}$ sample. This dynamic reset of the sensor orientation will allow the accumulated drift error to be removed or minimized. As mentioned earlier, each sample contains a random noise element that results in a linear error accumulation that increases with time.

Eventually, the accumulated errors in the calculation of the current sample $\varphi$ and $\theta$ angles result in an increasing error in subtracting the gravity component from the current sample accelerometer data. Eventually, this accumulated error will render the calculated speed and distance useless. If the aforementioned sample is detected, it is preferred to recalculate the $\varphi$ and $\theta$ via the $0^{th}$ sample method and NOT simply add the incremental angle associated with the Nth sample to the N-$1^{th}$ angle.

Additional signal enhancement can be achieved by using a linear interpolation technique to reduce the error in the calculated angles between successive static samples. Various known in the art techniques can be employed to post-process out this accumulated error resulting in considerable improvement in signal quality.

The wireless internet smart device 26 referred to in FIG. 6 may be a smart computer device in one of many forms. In one favored form, the computer is a smartphone or tablet or iPod Touch $5^{th}$ Generation® or higher. The primary requirement for the smart computer device 26 is that it can support data transmission by having a built in Bluetooth® enabled protocol such as Bluetooth® 4.0 or higher and BLE. Similarly, a smart laptop having built-in Bluetooth protocols, such as Bluetooth 3 or 4 or a smart HD flat panel television may be used as the smart computer device 26. The smart computer device may be a smartphone, laptop, tablet, etc. to provide long range data transport via any Wi-Fi or cellular provider to the website 33. The smart computer device provides long range data transport via any Wi-Fi or cellular provider to the fitness website. Some program apps are downloaded on line to the smart computer device to complement preloaded program apps.

It is intended by the use of the word "Combine" to cover all forms of sport activities from the professional level to the grade school, high school, college and minor league levels and not just the professional American /Canadian football sports. It would be readily apparent to those skilled in the art that the teachings of this invention are applicable to the fitness training in the sports of soccer, baseball, field and ice hockey and basketball. The invention is also applicable to all forms of individual exercises such as dancing, ice figure skating, the games of Summer, Winter, and Special Olympics, yoga, plyometrics, calisthenics, rowing, and a mix thereof, such as by way of examples cross training and triathlons. The invention is also applicable to many activities requiring fitness training for physical strength and endurance such as bicycle racing, marathons, swimming, surfing, scuba diving, beach and water volleyball, tennis, golf, hiking and mountain climbing. Benefits of the invention are available to those engaged in activities such as boxing, wrestling, hang gliding, sail surfing, bull fighting, the running of the bulls (running with the bulls), rodeo events, weightless fitness exercising in space, fencing, and hunting. Conditioning for all forms of sports and other indoor or outdoor activities may benefit from the invention.

Those individuals engaged in rehabilitation exercises and those trying to lose weight or build body mass also may benefit from the health advantages set forth by the invention.

In the instant specification, it is to be understood that the terms "sensor module", "universal sensor module", "universal sensor motion module", "universal exercising motion sensor module" and "universal motion exercising sensor module" may be used interchangeably as all the modules contain the 6-DOF mems motion detecting sensor with attendant motion coded algorithms.

As used herein, the terms "include", "including", "for example", "e.g." and variations thereof, are not intended to be terms of limitation, but rather to be followed by the words "without limitation". Various modifications to the preferred embodiments and the generic terms, principles, features and advantages of the present invention expressed in the written description and figures should not be limited to the exact construction and operation as illustrated and described. Many modifications, changes and equivalents will be readily apparent to those skilled in the art and are intended to fall within the scope of the invention which is not intended to be limited to the embodiments disclosed but is to be accorded the widest scope consistent with the principles and features described herein.

What is claimed is:

1. A method of gathering biometric raw data generated by an individual exercising and sending the biometric raw data to a fitness website wherein the gathering of the biometric raw data includes the following steps:
    the step of the individual selecting from at least one exercise mode of specific exercises presented by the fitness website in response to fitness goals communicated by the individual to the fitness website;
    the step of the individual using a smart computer device for viewing and/or listening to exercise instructions of how the specific exercises are performed as taught by video podcasts generated by the fitness website;
    the further step of the individual wearing a universal motion exercising sensor module having a 6-DOF sensor while exercising to gather the biometric raw data;
    the further step of the individual repeating as instructed a number of repetitions of the specific exercises wherein the number of repetitions is selected by the fitness website; and
    the further step of the individual sending the gathered biometric raw data to the fitness website by using the smart computer device or other smart computer device.

2. The method of claim 1 wherein the individual does the step of performing specific exercises in the form of standard exercises used for conditioning /comparing purposes by an athletic sports combine.

3. The method of claim 2 comprising:
    the further step of the fitness website using motion algorithms as applied to the biometric raw data generated from the exercises performed by the individual to compute at least five of:
    Reps (each individual rep during exercise)
    Sets (each set that is done per exercise)
    40 yard dash (10, 20, 30 and 40 yard increments)
    60 to a100 yard dash
    Vertical jump
    Horizontal/Broad jump
    Short/20 yard dash
    RAST (Repeated anaerobic Sprint Test)
    Calories burned
    Steps taken
    Distance traveled
    Velocity and Acceleration.

4. The method of claim 1 further comprising:
    the step of the fitness website using motion algorithms as applied to the raw data generated by the individual in combination with a MET NUMBER based on the metabolic equivalent to exercise calories for each different type of exercise and intensity level of exercise performed by the individual to measure calories burned by the individual.

5. The method of claim 4 further comprising:
    the step of the fitness website using the biometric raw data to compute calories burned for each exercise completed and further computing an overall total daily calorie burn based on all biometric raw data sent to the fitness website.

6. The method of claim 1 further comprising:
    the step of the individual placing the universal motion exercising sensor module in a cradle affixed to a weight lifted or moved as one of the specific exercises provided by the fitness website.

7. The method of claim 6 further comprising:
    the step of the individual manually entering the weight lifted or moved in pounds or kilograms in the smart computer device or other smart computer device.

8. The method of claim 1 comprising:
    the further step of the fitness website instructing the individual to conduct specific weight strength exercises after placing the universal motion sensor exercising module on the wrist, leg and chest of the individual and;
    the further step of the fitness website calculating Peak Power assessment of the individual based on the biometric raw data generated by the individual doing the specific weight strength exercises.

9. The method of claim 8 comprising:
    the further step of the fitness website calculating for specific weight lifting exercises weights to be lifted and reps thereof for the individual based on a one rep max number derived from the Peak Power assessment.

10. The method of claim 8 comprising:
    the further step of the fitness website calculating for the individual unload weights and reps thereof based on the specific weight lifting exercises completed by the individual.

11. The method of claim 1 comprising:
    the further step of the fitness website instructing the individual while wearing the universal motion exercising sensor module about the chest to complete a series of pushups per unit of time with the first pushup measured by the distance raised above the ground and the velocity of the pushup to determine Pushup Peak Power of the individual.

12. The method of claim 11 further comprising:
    the further step of the fitness website based on the Pushup Peak Power calculating for the individual Maximal Pushups per Minute along with a recommended repetition number of pushups for the individual over a selected minute interval.

13. The method of claim 1 comprising:
    the further step of the fitness website instructing the individual to wear a heart rate monitor to determine heart rate while wearing the universal motion exercising sensor module about the chest; and the further step of instructing the individual to perform a cardiovascular fitness assessment exercise; and the further step of the fitness website calculating based on both the biometric raw data generated from the cardiovascular fitness assessment exercise and the heart rate to determine heart rate numbers at VT/AT and Peak VO2.

14. The method of claim 13 comprising:

the further step of the fitness website calculating the optimal period of training times for the individual based on the ventricle threshold number VT and/or the anaerobic threshold number AT.

15. The method of claim 1 comprising:

the further step of the fitness website calculating at least one of a "J-Score" for the individual for each exercise completed based on age and gender and an overall "J-Score" based on the average of types of specific exercises completed.

* * * * *